US007910609B2

(12) United States Patent
DeGrado et al.

(10) Patent No.: US 7,910,609 B2
(45) Date of Patent: Mar. 22, 2011

(54) INHIBITORS OF INTEGRIN ALPHA2BETA1 WITH MODIFIED UREA MOIETY

(75) Inventors: William F. DeGrado, Media, PA (US); Seth E. Snyder, Hackensack, NJ (US); Meredith W. Miller, Philadelphia, PA (US); Sandeep Basra, Munich (DE); Joel S. Bennett, Bryn Mawr, PA (US); Sungwook Choi, San Diego, CA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/237,015

(22) Filed: Sep. 24, 2008

(65) Prior Publication Data

US 2009/0197861 A1     Aug. 6, 2009

Related U.S. Application Data

(63) Continuation of application No. 11/916,746, filed as application No. PCT/US2006/022225 on Jun. 7, 2006.

(60) Provisional application No. 60/687,972, filed on Jun. 7, 2005.

(51) Int. Cl.
| | |
|---|---|
| A01N 43/00 | (2006.01) |
| A61K 31/397 | (2006.01) |
| C07D 277/00 | (2006.01) |
| C07D 205/00 | (2006.01) |

(52) U.S. Cl. .................. 514/327; 548/200; 548/953
(58) Field of Classification Search .................. None
See application file for complete search history.

(56) References Cited

U.S. PATENT DOCUMENTS

| | | | |
|---|---|---|---|
| 6,096,707 | A | 8/2000 | Heino et al. |
| 6,369,034 | B1 | 4/2002 | Doherty et al. |
| 6,423,688 | B1 | 7/2002 | Thorsett et al. |
| 6,645,939 | B1 | 11/2003 | Durette et al. |
| 6,734,311 | B2 | 5/2004 | Hagmann et al. |
| 6,900,179 | B2 | 5/2005 | Thorsett et al. |
| 6,943,180 | B2 | 9/2005 | Doherty et al. |
| 2003/0100585 | A1 | 5/2003 | Duplantier et al. |
| 2004/0072850 | A1 | 4/2004 | Knegtel et al. |

FOREIGN PATENT DOCUMENTS

| | | |
|---|---|---|
| WO | WO 03/008380 A1 | 1/2003 |
| WO | WO 2006/133338 A1 | 12/2006 |
| WO | WO 2007/027742 A2 | 3/2007 |

OTHER PUBLICATIONS

Ettmayer et al. Lessons Learned from Marketed and Investigational Prodrugs. J Med Chem 2004, vol. 47, No. 10, pp. 2393-2404.*
Han et al. Targeted Prodrug Design to Optimize Drug Delivery. AAPS Pharmsci 2000. vol. 2, No. 1, article 6, p. 1.*
Testa. Prodrug research: futile or fertile? biochem Pharmacol. 2004, vol. 68, pp. 2097-2106.*
Vippagunta et al. Crystalline solids. Adv. Drug Delivery Reviews. 2001, vol. 48, pp. 3-26.*
Baronas-Lowell D, Lauer-Fields JL, Borgia JA, Sferrazza GF, Al-Ghoul M, Minond D, Fields GB. Differential Modulation of Human Melanoma Cell Metalloproteinase Expression by Alpha2Beta1 Integrin and CD44 Triple-Helical Ligands Derived from Type IV Collagen. J Biol Chem. 279(42), 43503-13, 2004.
Bellavite, P. A., G.; Guzzo, P.; Arigliano, P.; Chirumbolo, S.; Manzato, F.; Santonastaso, C. A Colorimetric Method for the Measure of Platelet Adhesion in Microtiter Plates. Anal. Biochem. 1994, 216, 444-450.
Bennett, J. S. a. V., G. Exposure of platelet fibrinogen receptors by ADP and epinephrine. J. Clin. Invest. 1979, 64, 1393-1401.
Bennett, J. S. C., C.; Vilaire, G.; Mousa, S. A.; DeGrado, W. F. Agonist-Activated alphavbeta3 on Platelets and Lymphocytes Binds to the Matrix Protein Osteopontin. J. Biol. Chem. 1997, 272, 8137-8140.
Bennett, J. S. Structure and function of the platelet integrin alphaIIb-beta3. J. Clin. Invest. 2005, 115, 3363-3369.
Chen et al, "EvidenceThat Ligand and Metal Ion Binding to Integrin a4b1 Are Regulated through a Coupled Equilibrium," The Journal of Biological Chemistry, 276(39), 36520-36529.
Chen H, Kahn ML. Reciprocal signaling by integrin and nonintegrin receptors during collagen activation of platelets. Mol Cell Biol. 23(14):4764-77, 2003.
Choi, S. V., G.; Marcinkiewicz, C.; Winkler, J. D.; Bennett, J. S.; DeGrado, W. F. . Small Molecule Inhibitors of Integrin alpha2beta1. J. Med. Chem. 2007, 50, 5457-5462.
Connors, W. L. J., J.; White, D. J.; Puranen, J. S.; Kankaanpaa, P.; Upla, P.; Tulla, M.; Johnson, M. S.; Heino, J. Two synergistic activation mechanisms of integrin alpha2beta1 integrin-mediated collagen binding. J. Biol. Chem. 2007, 282, 14675-14683.
DeWood, M. A. S., J.; Notske, R.; Mouser, L. T.; Burroughs, R.; Golden, M. S.; Lang, K. T. . Prevalence of Total Coronary Occlusion During the Early Hours of Transmural Myocardial Infarction. N. Eng. J. Med. 1980, 303, 897-902.
Emsley J, Knight CG, Farndale RW, Barnes MJ, Liddington RC. Structural Basis of Collagen Recognition by Integrin Alpha2Beta1. Cell. 101(1), 47-56, 2000.
Emsley, J. K., S. L.; Bergelson, J. M.; Liddington, R. C. Crystal Structure of the I Domain from Integrin alpha2beta1. J. Biol. Chem. 1997, 273, 28512-28517.
Falk, E, Shah, P.K. & Fuster, V. Coronary Plaque Disruption. Circulation 92, 657-671 (1995).
Feire AL, Koss H, Compton T. Cellular Integrins Function as Entry Receptors For Human Cytomegalovirus Via a Highly Conserved Disintegrin-Like Domain. Proc Natl Acad Sci U S A. 101(43), 15470-5, 2004.
Ferarra, N. The Role of Vascular Endothelial Growth Factor in Pathological Angiogenesis. Breast Cancer Res Treat. 36(2), 127-37, 1995.
Folkman J. Angiogenesis in Cancer, Vascular, Rheumatoid and Other Disease. Nat Med. 1(1), 27-31, 1995.
Furihata, K. N., D. J.; Kunicki, T. J. Influence of platelet collagen receptor polymorphisms on risk for arterial thrombosis. Arch. Pathol. Lab. Med. 2002, 126, 305-309.

(Continued)

*Primary Examiner* — Marcela M Cordero Garcia
(74) *Attorney, Agent, or Firm* — Woodcock Washburn, LLP

(57) ABSTRACT

Novel compounds inhibiting the integrin α2β1/GPIa-IIa receptor are disclosed. Also disclosed are pharmaceutical compositions containing the compounds, as well as methods of their therapeutic use. The compounds disclosed are useful, inter alia, as inhibitors of integrin α2β1/GPIa-IIa-mediated activity.

34 Claims, No Drawings

OTHER PUBLICATIONS

Fuster, V., Badimon, L., Badimon, J.J. & Chesebro, J.H. The Pathogenesis of Coronary Artery Disease and the Acute Coronary Syndromes (1). N. Engl. J. Med. 326, 242-250, 1992.
Graham KL, Halasz P, Tan Y, Hewish MJ, Takada Y, Mackow ER, Robinson MK, Coulson BS. Integrin-using rotaviruses bind alpha2beta1 integrin alpha2 I domain via VP4 DGE sequence and recognize alphaXbeta2 and alphaVbeta3 by using VP7 during cell entry. J Virol. 77(18), 9969-78, 2003.
Hagmann, W.K., The discovery and potential of N-sulfonylated dipeptide VLA-4 antagonists. Curr. Top Med. Chem., 2004, 4(14), 1461-1471.
Han J, Jenq W, Kefalides NA. Integrin Alpha2Beta1 Recognizes Laminin-2 and Induces C-erb B2 Tyrosine Phosphorylation in Metastatic Human Melanoma Cells. Connect Tissue Res. 40(4), 283-93, 1999.
Handa, M., ; Watanabe, K.; Kawai, Y.; Kamata, T.; Koyama, T.; Nagai, H.; Ikeda, Y. Platelet unresponsiveness to collagen: involvement of glycoprotein Ia-IIa (alpha2beta1 integrin) deficiency associated with a myeloproliferative disorder. Thromb. Haemost. 1995, 73, 521-528.
He L, Pappan LK, Grenache DG, Li Z, Tollefsen DM, Santoro SA, Zutter MM. The contributions of the alpha 2 beta 1 integrin to vascular thrombosis in vivo. Blood. 102(10):3652-7, 2003.
Holtkotter, O. N., B.; Smyth, N.; Muller, W.; Hafner, M.; Schulte, V.; Krieg, T.; Eckes, B. Integrin alpha2-deficient mice develop normally, are fertile, but display partially defective platelet interaction with collagen. J. Biol. Chem. 2002, 277, 10789-10794.
Huryn, D.M. et al., The identification and optimization of orally efficacious, small molecule VLA-4 antagonists. Curr. Top. Med. Chem., 2004, 4(14), 1473-1484.
Huryn, D.M. et al., Synthesis, characterization and evaluation of pro-drugs of VLA-4 antagonists. Bioorg. Med. Chem Lett., Apr. 5, 2004, 14(7), 1651-1654 Erratum in: Bioorg Med Chem Lett. Nov. 1, 2004;14(21):5449.
Hynes RO. Integrins: bidirectional, allosteric signaling machines. Cell. 110(6):673-87. Review, 2002.
Inoue, O. et al., Integrin alpha2beta1 mediates outside-in regulation of platelet spreading on collagen through activation of Src Kinases and PLCgamma2. J. Cell Biol. 160(5): 769-80 (2003).
Jackson SP and Schoenwaelder SM. Antiplatelet Therapy: In Search of the 'Magic Bullet'. Nat. Rev. Drug. Discov. 2(10), 775-89, 2003.
Jung SM, Moroi M. Platelets interact with soluble and insoluble collagens through characteristically different reactions. J Biol Chem. 273(24):14827-37, 1998.
Jung, S. M. A. M., M. Signal-transducing mechanisms involved in activation of the platelet collagen receptor integrin alpha2beta1. J. Biol. Chem. 2000, 275, 8016-8026.
Kamenecka TM, Lanza T Jr, de Laszlo SE, Li B, McCauley ED, Van Riper G, Egger LA, Kidambi U, Mumford RA, Tong S, MacCoss M, Schmidt JA, Hagmann WK. N-aryl-prolyl-dipeptides as potent antagonists of VLA-4. Bioorg Med Chem Lett. Aug. 19, 2002;12(16):2205-8.
Kehrel, B. B., L.; Kokott, R.; Mesters, R.; Stenzinger, W.; Clemetson, K. J.; van der Loo, J. Deficiency of intact thrombospondin and membrane glycoprotein Ia in platelets with defective collagen-induced aggregation and spontaneous loss of disorder. Blood 1988, 71, 1074-1078.
Knight, C.G. et al., The collagen-binding A-domains of integrins alpha(1)beta(1) and alpha(2)beta(1) recognize the same specific amino acid sequence, GFOGER, in native (triple-helical) collagens. J. Biol. Chem., 2000, 275, 35-40.
Knutson JR, Iida J, Fields GB, McCarthy JB. CD44/Chondroitin Sulfate Proteoglycan and Alpha 2 Beta 1 Integrin Mediate Human Melanoma Cell Migration on Type IV Collagen and Invasion of Basement Membranes. Mol Biol Cell. 7(3), 383-96, 1996.
Koo, G.C. et al., A small molecule very late antigen-4 antagonist can inhibit ovalbumin-induced lung inflammation. Am. J. Respir. Crit. Care Med., May 15, 2003, 167(10), 1400-1409.
Kritzik M, Savage B, Nugent DJ, Santoso S, Ruggeri ZM, Kunicki TJ. Nucleotide polymorphisms in the alpha2 gene define multiple alleles that are associated with differences in platelet alpha2 beta1 density. Blood. 92(7):2382-8 (1998).
Kufrin, D. et al., "Antithrombotic thrombocytes: ectopic expression of urokinase-type plasminogen activator in platelets," Blood, 2003, 102(3), 926-933.
Kuijpers, M.J. et al., Complementary roles of glycoprotein VI and alpha2beta1 integrin in collagen-induced thrombus formation in flowing whole blood ex vivo. FASEB J., 2003, 17(6), 685-687.
Kumar R. Aseptic meningitis: Diagnosis and management. Indian J Pediatr. 72(1), 57-63, 2005.
Kunicki, T. J. O., R.; Annis, D.; Honda, Y. Variability of integrin alpha2beta1 activity on human platelets. Blood 1993, 82, 2693-2703.
Leone et al., "An Assessment of the Mechanistic Differences Between Two Integrin a4b1 Inhibitors, the Monoclonal Antibody TA-2 and the Small Molecule BIO5192, in Rat Experimental Autoimmune Encephalomyelitis," The Journal of Pharmacology and Experimental Therapeutics, 305(3), 1150-1162.
Lin LS, Lanza TJ Jr, Castonguay LA, Kamenecka T, McCauley E, Van Riper G, Egger LA, Mumford RA, Tong X, MacCoss M, Schmidt JA, Hagmann WK. Bioisosteric replacement of anilide with benzoxazole: potent and orally bioavailable antagonists of VLA-4. Bioorg Med Chem Lett. May 3, 2004;14(9):2331-4.
Londrigan SL, Graham KL, Takada Y, Halasz P, Coulson BS. Monkey rotavirus binding to alpha2beta1 integrin requires the alpha2 I domain and is facilitated by the homologous beta1 subunit. J Virol. 77(17), 9486-501, 2003.
Lu, C. S., M.; Zang, Q.; Takagi, J.; Springer, T. A. Locking in Alternate Conformations of the Integrin aLb2 I Domain with Disulfide Bonds Reveals Functional Relationships Among Integrin Domains. PNAS 2001, 98, 2393-2398.
Luo, B.-H. C., C. V.; Springer, T. A. Structural basis of integrin signaling and regulation. Annu. Rev. Immunol. 2007, 25, 619-647.
Nieswandt B, Brakebusch C, Bergmeier W, Schulte V, Bouvard D, Mokhtari-Nejad R, Lindhout T, Heemskerk JW, Zirngibl H, Fassler R. Glycoprotein VI But Not Alpha2Beta1 Integrin is Essential For Platelet Interaction With Collagen. EMBO J. 20(9), 2120-30, 2001.
Nieswandt B, et al. (2001); Ruggeri ZM. Platelets In Atherothrombosis. Nat Med. 8(11), 1227-34, 2002.
Nieswandt B, Watson SP. Platelet-Collagen Interaction: Is GPVI the Central Receptor? Blood. 102(2), 449-6, 2003.
Nieuwenhuis HK, Sakariassen KS, Houdijk WP, Nievelstein PF, Sixma JJ. Deficiency of Platelet Membrane Glycoprotein Ia Associated With a Decreased Platelet Adhesion to Subendothelium: A Defect in Platelet Spreading. Blood. 68(3), 692-5, 1986.
Nieuwenhuis, H. K. A., J. W. N.; Houdijk, W. P. M.; Sixma, J. J. Human blood platelets showing no response to collagen fail to express surface glycoprotein Ia. Nature 1985, 318, 470-472.
Onley DJ, Knight CG, Tuckwell DS, Barnes MJ, Farndale RW. Micromolar Ca2+ concentrations are essential for Mg2+-dependent binding of collagen by the integrin alpha 2beta 1 in human platelets. J Biol Chem. 275(32):24560-4, 2000.
Pepinsky RB, Mumford RA, Chen LL, Leone D, Amo SE, Riper GV, Whitty A, Dolinski B, Lobb RR, Dean DC, Chang LL, Raab CE, Si Q, Hagmann WK, Lingham RB. Comparative assessment of the ligand and metal ion binding properties of integrins alpha9beta1 and alpha4beta1. Biochemistry. Jun. 4, 2002;41(22):7125-41.
Rosamond, W. F., K.; Furie, K.; Go, A.; Greenlund, K.; Haase, K.; Hailpern, S. M.; Ho, M.; Howard, V.; Kissela, B.; Kittner, S.; Lloyd-Jones, D.; McDermott, M.; Meigs, J.; Moy, C.; Nichol, G.; O'Donnell, C.; Roger, V.; Sorlie, P.; Steinberger, J.; Thom, T.; Wilson, M; Hong, Y.. Heart disease and stroke statistics 2008 update. A report from the American Heart Association. Circulation Prepublished online: Dec. 17, 2007, DOI: 10.1161/CIRCULATIONAHA.107.187998.
Saelman, E. U. M. N., H. K.; Hese, K. M.; de Groot, P. G.; Heijnen, H. F. G.; Sage, E. H.; Williams, S.; McKeown, L.; Gralnick, H. R.; Sixma, J. J. Platelet Adhesion to Collagen Types I through VIII Under Conditions of Stasis and Flow is Mediated by GPIa/IIIa (alpha2beta1-Integrin). Blood 1994, 83, 1244-1250.
Santoro SA. Identification of a 160,000 Dalton Platelet Membrane Protein That Mediates the Initial Divalent Cation-dependent Adhesion of Platelets to Collagen. Cell. 46(6), 913-20, 1986.

Santoro, S. A. Platelet Surface Collagen Polymorphisms: Variable Receptor Expression and Thrombotic/Hemorrhagic Risk. Blood 1999, 93, 3575-3577.

Savage B, Ginsberg MH, Ruggeri ZM. Influence of Fibrillar Collagen Structure on the Mechanisms of Platelet Thrombus Formation Under Flow. Blood. 94(8), 2704-15, 1999.

Senger DR, Perruzzi CA, Streit M, Koteliansky VE, de Fougerolles AR, Detmar M. The Alpha(1)Beta(1) and Alpha(2)Beta(1) Integrins Provide Critical Support For Vascular Endothelial Growth Factor Signaling, Endothelial Cell Migration, and Tumor Angiogenesis. Am J Pathol. 160(1), 195-204, 2002.

Senger DR, Van de Water L, Brown LF, Nagy JA, Yeo KT, Yeo TK, Berse B, Jackman RW, Dvorak AM, Dvorak HF. Vascular Permeability Factor (VPF, VEGF) in Tumor Biology. Cancer Metastasis Rev. 12(3-4), 303-24, 1993.

Shattil, S. J. a. N., P. J. Integrins: Dynamic Scaffolds for Adhesion and Signaling in Platelets. Blood 2004, 104, 1606-1615.

Shimaoka M, Salas A, Yang W, Weitz-Schmidt G, Springer TA. Small molecule integrin antagonists that bind to the beta2 subunit I-like domain and activate signals in one direction and block them in the other. Immunity. 19(3):391-402, 2002.

Siljander PR, Munnix IC, Smethurst PA, Deckmyn H, Lindhout T, Ouwehand WH, Farndale RW, Heemskerk JW. Platelet receptor interplay regulates collagen-induced thrombus formation in flowing human blood. Blood. 103(4):1333-41, 2004.

Stasiak M, Mehlin C, Boni E, Vaisar T, Little T, Kim HO, Qabar M. Sulphonamide-based small molecule VLA-4 antagonists. Bioorg Med Chem Lett. Nov. 3, 2003;13(21):3875-8.

Sweeney SM, DiLullo G, Slater SJ, Martinez J, Iozzo RV, Lauer-Fields JL, Fields GB, San Antonio JD. Angiogenesis in Collagen I Requires Alpha2Beta1 Ligation of a GFP*GER Sequence and Possibly p38 MAPK Activation and Focal Adhesion Disassembly. J Biol Chem. 278(33), 30516-24, 2003.

Takagi, J. P., B. M.; Walz, T.; Springer, T. A. Global conformational rearrangements in integrin extracellular domains in outside-in and inside-out signaling. Cell 2002, 110, 599-611.

Tam, S. H. S., P. M.; Jordan, R. E.; Nakada, M. T. Abciximab (ReoPro, chimeric 7E3 Fab) demonstrates equivalent affinity and functional blockade of glycoprotein IIb/IIIa and alphavbeta3 integrins. Circulation 1998, 98, 1085-1091.

Triantafilou K & Triantafilou M. A biochemical approach reveals cell-surface molecules utilised by Picornaviridae: Human Parechovirus 1 and Echovirus 1. J Cell Biochem. 80(3), 373-81, 2001.

Tuckwell D, Calderwood DA, Green LJ, Humphries MJ. Integrin alpha 2 I-domain is a binding site for collagens. J Cell Sci. 108(Pt 4):1629-37, 1995.

Watson, S. P. a. G., J. Collagen receptor signaling in platelets: extending the role of the ITAM. Immunol. Today 1998, 19, 260-264.

Welzenbach, K. H., U.; Weitz-Schmidt, G. Small molecule inhibitors induce conformational changes in the I-domain and the I-like domain of lymphocyte function-associated antigen-1. J. Biol. Chem. 2002, 277, 10590-10598.

White, T. C. B., M. A.; Robinson, D. K.; Yin, H.; DeGrado, W. F.; Hanson, S. R.; McCarty, O. J. . The Leech Product Saratin is a Potent Inhibitor of Platelet Integrin alpha2beta1 and von Willebrand Factor Binding to Collagen. FEBS J. 2007, 274, 1481-1491.

Yang C, Zeisberg M, Lively JC, Nyberg P, Afdhal N, Kalluri R. Integrin Alpha1Beta1 and Alpha2Beta1 Are the Key Regulators of Hepatocarcinoma Cell Invasion Across the Fibrotic Matrix Microenvironment. Cancer Res. 63(23), 8312-7, 2003.

U.S. Appl. No. 11/916,746 by William F. DeGrado et al., filed Dec. 9, 2008.

U.S. Appl. No. 61/099,747 by William F. DeGrado, et al., filed Sep. 24, 2008.

U.S. Appl. No. 60/687,972 by William F. DeGrado, et al., filed Jun. 7, 2005.

U.S. Appl. No. 60/712,775 by Seth E. Snyder, et al., filed Aug. 31, 2005.

* cited by examiner

INHIBITORS OF INTEGRIN ALPHA2BETA1 WITH MODIFIED UREA MOIETY

CROSS-REFERENCE TO RELATED APPLICATIONS

This application is a continuation of U.S. Ser. No. 11/916,746, filed Dec. 9, 2008, which is the U.S. national stage entry of PCT/US2006/022225, filed Jun. 7, 2006, which claims priority from U.S. Provisional App. No. 60/687,972, filed Jun. 7, 2005.

GOVERNMENT RIGHTS

The United States Government may have rights in the invention described herein, which was made in part with funding from the National Center for Research Resources (U.S. National Institutes of Health), Grant No. UL1RR024134.

TECHNICAL FIELD

The present invention relates to "small" molecule inhibitors of the α2β1/GPIa-IIa integrin, as well as methods of production, use, and therapeutic administration thereof.

BACKGROUND

Recruitment, adhesion, and aggregation of platelets at sites of vascular injury are critical to generation of beneficial blood clotting events. However, excessive accumulation of platelets, e.g., at sites of ruptured atherosclerotic plaques, can give rise to the development of acute coronary syndromes, stroke, ischaemic complications of peripheral vascular disease, and other disease states. Fuster, V., Badimon, L., Badimon, J. J. & Chesebro, J. H. *The Pathogenesis of Coronary Artery Disease and the Acute Coronary Syndromes* (1). *N. Engl. J. Med.* 326, 242-250 (1992); Falk, E, Shah, P. K & Fuster, V. *Coronary Plaque Disruption. Circulation* 92, 657-671 (1995). Promise for enhanced clinical management of such vascular diseases has arisen in recent years with progress in understanding of the mechanisms underlying the formation of arterial plaque and thrombosis and of the criticality of the role of platelet activity in the development of cardiovascular disease.

Tempered by the understanding that antithrombotic treatment should be effective and yet avoid undermining hemostasis, clinicians of cardiovascular disease prevention and treatment have depended on mild therapeutic agents like aspirin and clopidogrel for widespread application. There are a variety of other antithrombotic drugs, including coumadin and abciximab (ReoPro®), ticlopidine, and others, but there remains an urgent need for newer and safer antithrombotics, to address stroke, deep vein thrombosis (DVT), myocardial infarction, coronary artery disease, cerebrovascular disease, peripheral arterial disease, diabetes mellitus, atrial fibrillation, congestive heart failure, and other vascular disorders. Jackson S P and Schoenwaelder S M. *Antiplatelet Therapy: In Search of the 'Magic Bullet'. Nat. Rev. Drug. Discov.* 2(10), 775-89 (2003). Review. More versatile and effective and yet selective and safe therapeutic agents are currently the object of extensive research worldwide, especially in light of the increasing prevalence of cardiovascular disease both due to changes in diet and lifestyle and in view of the aging of the population. Special emphasis has been placed on the issue of improving efficacy without compromising safety, since all forms of presently available antithrombotic therapies cannot be administered at potent doses without producing negative physiological conditions, primarily bleeding events.

Upon vessel injury and attendant removal or damage of the protective endothelial lining, platelets encounter a diverse set of proteins from the connective tissue of the vessel wall. These include collagen and von Willebrand factor (vWf). Platelet adhesion to these proteins and subsequent activation is mediated by a multitude of platelet receptors. Adhesion of platelets to the extracellular matrix triggers a series of signaling events that ultimately result in formation of a hemostatic plug known as a thrombus. Recent findings provide strong evidence that immediately following vessel rupture, the platelet receptor GPVI binds loosely to exposed collagen, which is alone insufficient to induce stable platelet adhesion, but which triggers a tyrosine kinase-based signaling pathway that results in major conformational changes and attendant activation in specific receptors, including integrin α2β1. Emsley J, Knight C G, Farndale R W, Barnes M J, Liddington R C. *Structural Basis of Collagen Recognition by Integrin Alpha2Beta1. Cell.* 101(1), 47-56 (2000).

Integrin α2β1, also known as platelet GPIa-IIa, was the first collagen receptor to be identified on platelets. Nieuwenhuis H K, Akkerman J W, Houdijk W P, Sixma J J. *Human Blood Platelets Showing No Response to Collagen Fail to Express Surface Glycoprotein Ia. Nature.* 318(6045), 470-2 (1985); Santoro S A. *Identification of a 160,000 Dalton Platelet Membrane Protein That Mediates the Initial Divalent Cation-dependent Adhesion of Platelets to Collagen. Cell.* 46(6), 913-20 (1986). Similar to other members of the integrin family, α2β1 links the cytoskeleton of the cell with the extracellular matrix. Hynes R O. *Integrins: bidirectional, allosteric signaling machines. Cell.* 110(6):673-87. Review (2002). Besides playing an essential role in adhesion to the extracellular matrix, integrins are indispensable for cellular signaling. All integrins are heterodimers, consisting of an α subunit and a β subunit. About half of the known mammalian integrins, including α2β1, have an I-domain inserted into the α subunit (Hynes, 2002). In these cases, the I-domain is responsible for binding of the integrin to its natural ligand(s). A specific amino acid sequence in collagen, GFOGER (O=hydroxyproline), promotes stable binding to the I-domain of α2β1. Onley D J, Knight C G, Tuckwell D S, Barnes M J, Farndale R W. *Micromolar Ca2+ concentrations are essential for Mg2+-dependent binding of collagen by the integrin alpha 2beta 1 in human platelets. J Biol Chem.* 275(32):24560-4 (2000). Binding occurs in a cation dependent manner, supported by either magnesium or manganese Tuckwell D, Calderwood D A, Green L J, Humphries M J. *Integrin alpha 2 I-domain is a binding site for collagens. J Cell Sci.* 108(Pt 4):1629-37 (1995). A crystal structure of a complex between the I-domain of α2β1 and a triple helical peptide containing the GFOGER sequence has been solved. Emsley J. Knight C G, Farndale R W, Barnes M J, Liddington R C. *Structural basis of collagen recognition by integrin alpha2beta1. Cell.* 101(1), 47-56 (2000). A glutamic acid (E) from the middle strand of the triple helix coordinates to metal-ion dependent adhesion site (MIDAS) while other residues of the GFOGER motif from the middle and trailing strands interact with complementary sites on the I-domain surface.

Importantly, integrin α2β1 has multiple states of activation which can be regulated from inside or outside of the cell. Hynes R O. *Integrins: bidirectional, allosteric signaling machines. Cell.* 110(6):673-87. Review (2002). For instance, signaling through the platelet receptor GPVI impinges upon the cytoplasmic domain of α2β1, which results in a dramatic conformational change that eventually propagates along the α2β1 integrin, ultimately affecting the I-domain at the integrin's head. Integrin activation is induced by several other platelet agonists, including ADP and thrombin. Jung S M, Moroi M. *Platelets interact with soluble and insoluble collagens through characteristically different reactions. J Biol. Chem.* 273(24):14827-37 (1998). The activated integrin can than bind tightly to collagen. This adhesion can potentially be blocked with either a direct competitor of the collagen/I-domain interaction or with an allosteric regulator, the latter of which precludes activation of the I domain. Two types of small-molecule inhibitors have been developed for a related integrin, αLβ2. Shimaoka M, Salas A, Yang W, Weitz-Schmidt G, Springer T A. *Small molecule integrin antagonists that bind to the beta2 subunit I-like domain and activate signals in one direction and block them in the other. Immunity.* 19(3):391-402 (2002). The first binds to the I-domain of αLβ2 at a distant site from the MIDAS, blocking activation of its I domain and subsequent binding to ICAM-1. The second binds to the I-like domain of the β subunit, which is located directly beneath the I domain. A direct competitive inhibitor of an I-domain/ligand interaction has not yet been reported.

Despite the fact that α2β1 integrin was discovered more than 15 years ago, its precise role in platelet adhesion and aggregation remains controversial. This is partially due to the overlapping functions of α2β1 and GPVI. Chen H, Kahn M L. *Reciprocal signaling by integrin and nonintegrin receptors during collagen activation of platelets. Mol Cell Biol.* 23(14): 4764-77 (2003). Integrin α2β1 is essential for platelet adhesion and activation on monomeric type I collagen; it has been demonstrated through platelet analysis that adhesion and thrombus growth on pepsin-solubilized type I collagen under low and high shear flow conditions is absolutely dependent on functional α2β1. Savage B, Ginsberg M H, Ruggeri Z M. *Influence of Fibrillar Collagen Structure on the Mechanisms of Platelet Thrombus Formation Under Flow. Blood.* 94(8), 2704-15 (1999); Nieswandt B, Brakebusch C, Bergmeier W. Schulte V, Bouvard D, Mokhtari-Nejad R, Lindhout T, Heemskerk J W, Zirngibl H, Fassler R. *Glycoprotein VI But Not Alpha2Beta1 Integrin is Essential For Platelet Interaction With Collagen. EMBO J.* 20(9), 2120-30 (2001). However, on the more physiologically relevant insoluble collagen (fibrillar collagen), α2β1 integrin may be dispensable, at least in the context of hemostasis. Nieswandt B, Watson S P. *Platelet-Collagen Interaction: Is GPVI the Central Receptor? Blood.* 102(2), 449-6 (2003). Review. For instance, fibrillar collagen-induced aggregation of β1-null mouse platelets is not reduced, despite a slight time delay. Nieswandt B, Brakebusch C, Bergmeier W. Schulte V, Bouvard D, Mokhtari-Nejad R, Lindhout T, Heemskerk J W, Zirngibl H, Fassler R. *Glycoprotein VI But Not Alpha2Beta1 Integrin is Essential For Platelet Interaction With Collagen. EMBO J.* 20(9), 2120-30 (2001). Furthermore, the β1-null platelets adhere normally to fibrillar collagen under static conditions. Nonetheless, it has been established that adhesion under physiological conditions of blood flow requires a functional α2β1 integrin. Siljander P R, Munnix I C, Smethurst P A, Deckmyn H, Lindhout T, Ouwehand W H, Farndale R W, Heemskerk J W. *Platelet receptor interplay regulates collagen-induced thrombus formation in flowing human blood. Blood.* 103(4): 1333-41 (2004).

Studies of platelets derived from two individuals with an integrin α2β1 deficiency have demonstrated a defect in adhesion and spreading on the subendothelium. Nieswandt B, et al. (2001); Ruggeri Z M. *Platelets In Atherothrombosis. Nat. Med.* 8(11), 1227-34 (2002). Review. Indeed, these patients exhibit only modest degree of defect in hemostasis, manifested as only minor bleeding complications. Nieuwenhuis H K, et al., *Nature.* 318(6045), 470-2 (1985); Nieuwenhuis H K, Sakariassen K S, Houdijk W P, Nievelstein P F, Sixma J J. *Deficiency of Platelet Membrane Glycoprotein Ia Associated With a Decreased Platelet Adhesion to Subendothelium: A Defect in Platelet Spreading. Blood.* 68(3), 692-5 (1986). This has important implications for the search for antithrombotic therapies with favorable safety profiles. It suggests that antagonism of α2β1 integrin will have a beneficially mild antithrombotic effect; increasing amount of evidence indeed suggests that α2β1 may have a greater role in pathological thrombosis relative to normal hemostasis. This observation may reflect the fact that an increased amount of collagen accumulates in diseased blood vessels. For instance, the extracellular matrix around an atheroslerotic lesion is heavily enriched in collagens. Nieswandt B, et al, (2003). Besides providing an adhesive support for platelets, collagen sends potent prothrombotic signals into the cell through interaction with its platelet receptors. Overexpression of α2β1 integrin has been linked to cardiovascular disease in humans. Kritzik M, Savage B, Nugent D J, Santoso S, Ruggeri Z M, Kunicki T J. *Nucleotide polymorphisms in the alpha2 gene define multiple alleles that are associated with differences in platelet alpha2 beta1 density. Blood.* 92(7):2382-8 (1998). Furthermore, recent in vivo data indicates that α2β1-deficient mice have delayed thrombus formation following carotid artery injury. He L, Pappan L K, Grenache D G, Li Z, Tollefsen D M, Santoro S A, Zutter M M. *The contributions of the alpha 2 beta 1 integrin to vascular thrombosis in vivo. Blood.* 102 (10):3652-7 (2003). These data reveal a critical role for α2β1 in thrombosis. Hence, the α2β1 integrin is an important pharmacological target for cardiovascular diseases, and the resulting treatment is expected to be well-tolerated and provide long-term antithrombotic protection.

Equally significant, the α2β1 integrin may be a target for cancer, several types of viral infections, and other pathologies. Overexpression of α2β1 in various types of cancer cells, particularly in human melanoma cells and hepatocellular carcinomas, has been linked to tumor metastasis. Han J, Jenq W, Kefalides N A. *Integrin Alpha2Beta1 Recognizes Laminin-2 and Induces C-erb B2 Tyrosine Phosphorylation in Metastatic Human Melanoma Cells. Connect Tissue Res.* 40(4), 283-93 (1999). Yang C, Zeisberg M, Lively J C, Nyberg P, Afdhal N, Kalluri R, *Integrin Alpha1Beta1 and Alpha2Beta1 Are the Key Regulators of Hepatocarcinoma Cell Invasion Across the Fibrotic Matrix Microenvironment. Cancer Res.* 63(23), 8312-7 (2003). The α2β1 integrin is known to be the primary melanoma cell adhesion molecule for type IV collagen, indicating a key role for that integrin in pathological metastasis Knutson J R, Iida J, Fields G B, McCarthy J B. *CD44/Chondroitin Sulfate Proteoglycan and Alpha 2 Beta 1 Integrin Mediate Human Melanoma Cell Migration on Type IV Collagen and Invasion of Basement Membranes. Mol Biol Cell.* 7(3), 383-96 (1996). Ligand binding by the α2β1 integrin triggers a series of intracellular signaling events that ultimately result in the release of cytokines and proteases, both of which are beneficial for tumor cell progression. Baronas-Lowell D, Lauer-Fields J L, Borgia J A, Sferrazza G F, Al-Ghoul M, Minond D, Fields G B. *Differential Modulation of Human Melanoma Cell Metalloproteinase Expression by Alpha2Beta1 Integrin and CD44 Triple-Helical Ligands Derived from Type IV Collagen. J Biol Chem.* 279(42), 43503-13 (2004). Furthermore, antagonism of the α2β1 integrin suppresses angiogenesis. Senger D R, Perruzzi C A, Streit M, Koteliansky V E, de Fougerolles A R, Detmar M. *The Alpha(1)Beta(1) and Alpha(2)Beta(1) Integrins Provide Critical Support For Vascular Endothelial Growth Factor Signaling, Endothelial Cell Migration, and Tumor Angiogenesis. Am J Pathol.* 160(1), 195-204 (2002). This has profound implications since angiogenesis is involved in growth and metastasis of solid tumors, rheumatoid arthritis, diabetic retinopathy, and a variety of other important disease states. Folkman J. *Angiogenesis in Cancer, Vascular, Rheumatoid and Other Disease. Nat. Med.* 1(1), 27-31 (1995). Review; Senger D R, Van de Water L, Brown L F, Nagy J A, Yeo K T, Yeo T K, Berse B, Jackman R W, Dvorak A M, Dvorak H F. *Vascular Permeability Factor (VPF, VEGF) in Tumor Biology. Cancer Metastasis Rev.* 12(3-4), 303-24 (1993). Review; Ferarra, N. *The Role of Vascular Endothelial Growth Factor in Pathological Angiogenesis. Breast Cancer Res Treat.* 36(2), 127-37 (1995). Review. Specific blocking of α2β1 function halts capillary morphogenesis, the essential antecedent to angiogenesis, whereas blocking of related integrin dimers or monomer subunits does not similarly arrest morphogenesis. Sweeney S M, DiLullo G, Slater S J, Martinez J, Iozzo R V, Lauer-Fields J L, Fields G B, San Antonio J D. *Angiogenesis in Collagen I Requires Alpha2Beta1 Ligation of a GFP\*GER Sequence and Possibly p38 MAPK Activation and Focal Adhesion Disassembly. J Biol Chem.* 278(33), 30516-24 (2003). Antagonism of the α2β1 integrin also curbs haptotactic endothelial cell migration, Senger D R et al., a critical step in extravasation of tumor cells into secondary tissues.

It has also recently been shown that human cytomegalovirus (HCMV), which is extremely promiscuous and responsible for significant mortality, requires the presence of α2β1 to penetrate a cell. Feire A L, Koss H, Compton T. *Cellular Integrins Function as Entry Receptors For Human Cytomegalovirus Via a Highly Conserved Disintegrin-Like Domain. Proc Natl Acad Sci USA.* 101(43), 15470-5 (2004). Likewise, integrin α2β1 has been strongly implicated in rotavirus cell attachment and entry. Graham K L, Halasz P, Tan Y, Hewish M J, Takada Y, Mackow E R, Robinson M K, Coulson B S. *Integrin-using rotaviruses bind alpha2beta1 integrin alpha2 I domain via VP4 DGE sequence and recognize alphaXbeta2 and alphaVbeta3 by using VP7 during cell entry. J. Virol.* 77(18), 9969-78. (2003). Rotaviruses are leading causes of acute gastroenteritis in human infants and young children and animals around the globe. Id. It has been demonstrated that inhibition of the α2β1 integrin forestalls cell binding and infection by rotaviruses. Londrigan S L, Graham K L, Takada Y, Halasz P, Coulson B S. *Monkey rotavirus binding to alpha2beta1 integrin requires the alpha2 I domain and is facilitated by the homologous beta1 subunit. J. Virol.* 77(17), 9486-501 (2003). Similarly, viruses of the Piconaviridae family, such as Echovirus 1 (Echo1), have also been shown to utilize the α2β1 integrin during the cell-infection cycle. Triantafilou K & Triantafilou M. *A biochemical approach reveals cell-surface molecules utilised by Picornaviridae: Human Parechovirus 1 and Echovirus 1. J Cell Biochem.* 80(3), 373-81 (2001). Echo viruses are implicated in numerous human pathologies; for example, certain forms of aseptic meningitis and acute respiratory illness are known to be caused by the Echo-1 virus. See, e.g., Kumar R. *Aseptic meningitis: Diagnosis and management. Indian J Pediatr.* 72(1), 57-63 (2005).

Inhibition of the α2β1 integrin may prove effective in impeding binding and entry of these problematic and medically-significant viruses, and in treatment of cancers and other disease states concerning which α2β1 expression and functionality is a significant factor, and previous efforts have been made to provide compounds possessing α2β1 integrin inhibitory activity. See Takayanagi, M et al., WO 03/008380. As yet, however, there is an unfulfilled need in these respects.

SUMMARY

The present invention provides inhibitors of integrin α2β1 and methods for their synthesis and use.

In one aspect, provided are compounds having the formula I:

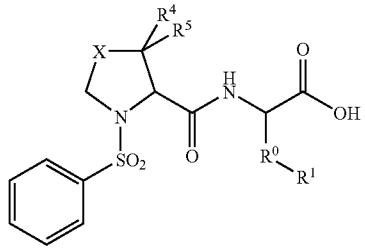

wherein:
X is $CH_2$, N, O, S, or a bond;
$R^0$ is alkylene;
$R^1$ is $-NHC(=O)R^2$ or $-NHC(=S)R^2$;
$R^2$ is $-NH(CHR^6)R^7$;
$R^4$ and $R^5$ are each independently H or $-CH_3$;
$R^6$ is H, alkyl, or aryl; and,
$R^7$ is alkyl, aryl, or aralkyl,
or a stereoisomer, partial stereoisomer, prodrug, pharmaceutically acceptable salt, hydrate, solvate, acid hydrate, or N-oxide thereof.

In another aspects, the present invention is directed to methods for treating at least one α2β1-affected disease state or infection comprising administering to a subject in need thereof a composition comprising a therapeutically effective amount of a compound having the formula I.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The present invention is directed to, among other things, "small" molecule inhibitors of the α2β1 integrin, as well as to methods of their use for treatment of the range of α2β1-affected disease states. These include, vascular conditions, diabetes- or rheumatoid arthritis-related conditions, cancers, viral infections, and other conditions or infections. The present invention represents a versatile and effective, yet selective and safe therapeutic regime for the treatment of α2β1-affected disease states, conditions, and infections.

The disclosures of each patent, patent application, and publication cited or described in this document are hereby incorporated herein by reference, in their entirety. Unless otherwise provided, superscript numbers appearing in brackets (i.e., "[x]") refer to the correspondingly-numbered publication listed in the final paragraph of the present application preceding the claims, each of which publications are hereby incorporated herein by reference in their entirety.

Integrin α2β1 consists of an α/β heterodimer that binds to collagen through its I-domain formed by the α chain.[13, 14] It can assume multiple conformations (from open high-affinity conformation to the closed low-affinity conformation) that are regulated through intracellular "outside-in" and "inside-out" signaling.[15, 16] The I-like domain at the interface of the α and β chains serves as an allosteric regulatory site by mediating the affinity of the I-domain for its ligand.[17, 18] Small molecule antagonists can bind the α/β interface and therefore force the α chain to remain in its low-affinity conformation.[17, 19, 21] While not intending to be bound by any particular theory of operation, it is believed that the compounds of the present invention may effect inhibition of the α2β1 integrin by targeting the integrin's I-like domain.

As employed above and throughout the disclosure, the following terms and abbreviations, unless otherwise indicated, shall be understood to have the following meanings.

"DAP" or "Dap" denotes 2,3-diaminopropionic acid.

"EDC" stands for 1-(3-Dimethylaminopropyl)-3-ethylcarbodiimide hydrochloride.

"HOBT" means 1-Hydroxybenzotriazole hydrate.

Protective groups are abbreviated according to the system disclosed in Greene, T. W. and Wuts, P. G. M., *Protective Groups in Organic Synthesis* 2d. Ed., Wiley & Sons, 1991, which is incorporated in its entirety herein. For example, "CBZ" or "Cbz" or "Z" stands for carbobenzyloxy or benzyloxycarbonyl, "Boc" or "BOC" represents t-butoxycarbonyl, "Alloc"/"Aloc" denotes allyloxycarbonyl, "Bz" means benzoyl, and "Fmoc" stands for 9-fluorenylmethoxycarbonyl.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compound and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the terms "component," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

The abbreviations in the specification correspond to units of measure, techniques, properties, or compounds as follows: "min" means minute(s), "g" means gram(s), "mg" means milligram(s), "μg" means microgram(s), "eq" means equivalent(s), "h" means hour(s), "μL" means microliter(s), "mL" means milliliter(s), "mM" means millimolar, "M" means molar, "mmol" or "mmole" means millimole(s), "cm" means centimeters, "SEM" means standard error of the mean, and "IU" means International Units. "IC$_{50}$ value" or "IC$_{50}$" means dose of the compound which results in 50% alleviation or inhibition of the observed condition or effect.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein).

"Amino" refers to —NH$_2$ and may include one or more substituents that replace hydrogen.

As used herein, "aryl", "arene", and "aromatic" each refer to an optionally substituted, mono-, di-, tri-, or other multicyclic aromatic ring system having from about 5 to about 50 carbon atom ring members (and all combinations and subcombinations of ranges and specific numbers of carbon atoms therein), with from about 6 to about 10 carbon ring atom members being preferred.

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

"Alkylidene" signifies

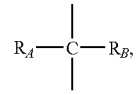

in which R$_A$ and R$_B$ are independently H or alkyl, and wherein alkyl is as previously defined.

As used herein, "aralkyl" refers to alkyl radicals bearing one or more aryl substituents and having from about 6 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms. In other preferred embodiments, the alkyl moieties have from about 1 to about 3 carbon atoms. Aralkyl groups may be optionally substituted.

"Alkylamino" signifies alkyl-(NH)—, wherein alkyl is as previously described and NH is defined in accordance with the provided definition of amino. "Arylamino" represents aryl-(NH)—, wherein aryl is as defined herein and NH is defined in accordance with the provided definition of amino. Likewise, "aralkylamino" is used to denote aralkyl-(NH)—, wherein aralkyl is as previously defined and NH is defined in accordance with the provided definition of amino. "Alkoxy" as used herein refers to the group R—O— where R is an alkyl group, and alkyl is as previously described. "Aralkoxy" stands for R—O—, wherein R is an aralkyl group as previously defined. "Alkylsulfonyl" means alkyl-SO$_2$—, wherein alkyl is as previously defined.

As used herein, "alkylene" refers to an optionally branched or substituted bivalent alkyl radical having the general formula —(CH$_2$)$_n$—, where n is 1 to 10, Non-limiting examples include methylene, trimethylene, pentamethylene, and hexamethylene.

As used herein, "heteroaryl" refers to an aryl radical wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members are preferred. Likewise, a "heterocyclic ring" may be an aryl radical wherein one or more of the carbon atom ring members is independently replaced by a heteroatom group selected from the group consisting of S, O, N, and NH. Heterocyclic rings having a total from about 5 to 14 carbon atom ring members and heteroatom ring members are preferred.

"Halo" and "halogen" each refers to a fluoro, chloro, bromo, or iodo moiety, with fluoro, chloro, or bromo being preferred.

The phrase reading "D is optional" means that the substituents to which D is attached may be directly attached to each other. For example, in some preferred embodiments, A is attached directly to E by a bond.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), oxo (=O), carboxy (—COOH), —O—C(=O)R", —C(=O)R", —OR", —C(=O)OR", -(alkylene)-C(=O)—OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (—SR"), sulfonic acid (—SO$_3$H), phosphonic acid (—PO$_3$H), —P(=O)(OR")OR", —S(=O)R", —S(=O)$_2$R", —S(=O)$_2$NH$_2$, —S(=O)$_2$NHR", S(=O)$_2$NR"R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Hydrate" refers to a compound of the present invention which is associated with water in the molecular form, i.e., in which the H—OH bond is not split, and may be represented, for example, by the formula R.H$_2$O, where R is a compound of the invention. A given compound may form more than one hydrate including, for example, monohydrates (R.H$_2$O) or polyhydrates (R.nH$_2$O wherein n is an integer>1) including, for example, dihydrates (R.2H$_2$O), trihydrates (R.3H$_2$O), and the like, or hemihydrates, such as, for example, R.n$_{/2}$H$_2$O, R.n$_{/3}$H$_2$O, R.n$_{/4}$H$_2$O and the like wherein n is an integer.

"Solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer>1) including, for example, disolvates (R.2(solvent)), trisolvates (R.3(solvent)), and the like, or hemisolvates, such as, for example, R.n$_{/2}$(solvent), R.n$_{/3}$(solvent), R.n$_{/4}$(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

The term "stereoisomers" refers to compounds that have identical chemical constitution, but differ as regards the arrangement of the atoms or groups in space.

"Racemic" means having the capacity for resolution into forms of opposed optical activity.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

"Prodrug" refers to compounds which are themselves inactive or minimally active for the activity desired, but through biotransformation can be converted into biologically active metabolites. For example, a prodrug of the present invention would include, inter alia, any compound which is convertible in vivo by metabolic means to a compound claimed or described in the present disclosure.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

As used herein, the terms "modulation" or "mediation" refer to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

In the present disclosure, the term "inhibitor" is intended to comprise any compound or agent, e.g., antibody, small molecule, peptide, oligopeptide, polypeptide, or protein, preferably small molecule or peptide, that exhibits a partial, complete, competitive and/or inhibitory effect by inhibiting, suppressing, repressing, or decreasing a specific activity, such as platelet activation or adhesion activity, stabilization of thromboses, metastasis, angiogenesis, or viral infection. In certain embodiments, the term preferably refers to an inhibitor of human pathological platelet activity, thus diminishing or blocking, preferably diminishing, some or all of the biological effects of pathological platelet activity. In certain other embodiments, the term preferably refers to an inhibitor of angiogenesis, metastasis, morphogenesis, matrix reorganization, cell migration, cell proliferation, cell colonization, or leukocyte infiltration. In still other embodiments, the term preferably refers to an inhibitor of viral infection.

The term "administering" means either directly administering a compound or composition of the present invention, or administering a prodrug, derivative or analog which will form an equivalent amount of the active compound or substance within the body.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

The term "vascular system" refers to the vessels and tissue that carry or circulate fluids in the body of an animal, including but not limited to the heart, blood vessels, lymphatic, pulmonary, and portal systems.

The phrases "vascular disease", "vascular disorder", "vascular condition", "vascular pathology", and the like, refer to bodily states affecting the channels and tissue that carry body fluids, such as, but not limited to stroke, deep vein thrombosis (DVT), myocardial infarction, coronary artery disease, cerebrovascular disease, peripheral arterial disease, diabetes mellitus, atrial fibrillation, congestive heart failure, acute coronary syndromes, stroke, pulmonary embolism, and ischaemic complications of peripheral vascular disease.

The term "angiogenesis" refers to the growth, formation, migration, infiltration, or proliferation of blood vessels.

"Piconaviridae viruses" are viruses belonging to the virus family Piconaviridae.

"Subject" or "patient" refers to an embryonic, immature, or adult animal, including the human species, that is treatable with the compositions, and/or methods of the present invention.

The disclosures of each patent, patent application, and publication cited or described in this document are hereby incorporated herein by reference, in their entirety.

The present invention is directed to, among other things, small-molecule inhibitors of the $\alpha 2\beta 1$ integrin and methods of their use for the treatment of certain vascular disorders and conditions, cancers, diabetes- and arthritis-related conditions, and viral infections. Because the activity of the disclosed compounds of formulas I is attributable to $\alpha 2\beta 1$ antagonism and otherwise provides inhibition of particular collagen-induced platelet activity, with respect to treatment of vascular conditions, administration thereof represents an extremely promising and heretofore unachieved strategy for safe antithrombotic therapy and treatment of other disease states associated with the vascular system. For example, it is believed that the present invention described presents a substantial breakthrough in the field of treatment, alleviation, inhibition, and/or prevention of such disorders and conditions, including, but not limited to, stroke, deep vein thrombosis (DVT), myocardial infarction, coronary artery disease, cerebrovascular disease, peripheral arterial disease, atrial fibrillation, and congestive heart failure, acute coronary syndromes, stroke, pulmonary embolism, and ischaemic complications of peripheral vascular disease. In an additional aspect, the present invention represents a promising and distinctive therapy for cancer and cancer-related conditions, including, but not limited to human melanoma, hepatocellular carcinoma, breast, lung, and ovarian cancers, pathological angiogenesis, metastasis, and leukocyte infiltration. In a still further aspect, the invention provides a means of treatment for diabetes- and arthritis-related ailments, such as rheumatoid arthritis, diabetic retinopathy, diabetes mellitus, and related conditions. Administration of the compounds of formula I also provides medicinal therapy as against viral infection, for example, by the human cytomegalovirus, rotaviruses, or Piconaviridae viruses, or susceptibility thereto.

In accordance with one embodiment of the present invention, provided are compounds having the formula I:

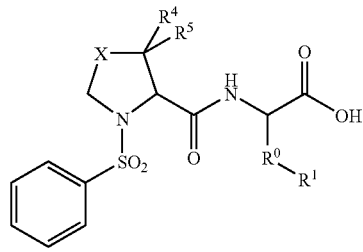

wherein:
$X$ is $CH_2$, N, O, S, or a bond;
$R^0$ is alkylene;
$R^1$ is —NHC(=O)$R^2$ or —NHC(=S)$R^2$;
$R^2$ is —NH(CHR$^6$)$R^7$;
$R^4$ and $R^5$ are each independently H or —$CH_3$;
$R^6$ is H, alkyl, or aryl; and,
$R^7$ is alkyl, aryl, or aralkyl, or a stereoisomer, partial stereoisomer, prodrug, pharmaceutically acceptable salt, hydrate, solvate, acid hydrate, or N-oxide thereof.

In other embodiments, the invention is directed to pharmaceutical compositions comprising a pharmaceutically-acceptable carrier, diluent, or excipient and a compound of formula I. Other embodiments of the invention provide compositions comprising a stereochemically enriched mixture of compounds of formula I.

In some embodiments, $R^4$ and $R^5$ are each —$CH_3$, X is S, and $R^0$ is —$CH_2$—. An exemplary compound is 2-[(3-Benzenesulfonyl-5,5-dimethyl-thiazolidine-4-carbonyl)-amino]-3-[3-(2,2-dimethyl-propyl)-ureido]-propionic acid. In such embodiments, $R^6$ may be H, and $R^7$ may be aryl or aralkyl. Such compounds include, inter alia, 2-[(3-Benzenesulfonyl-5,5-dimethyl-thiazolidine-4-carbonyl)-amino]-3-(3-cyclohexylmethyl-ureido)-propionic acid and 2-[(3-Benzenesulfonyl-5,5-dimethyl-thiazolidine-4-carbonyl)-amino]-3-[3-(2,2-diphenyl-ethyl)-ureido]-propionic acid. In certain embodiments, $R^7$ is aryl and $R^1$ is —NHC(=S)$R^2$. For example, the compound may be 2-[(3-Benzenesulfonyl-5,5-dimethyl-thiazolidine-4-carbonyl)-amino]-3-(3-benzyl-thioureido)-propionic acid. In certain other embodiments, $R^7$ is aralkyl. For example, the compound may be 2-[(3-Benzenesulfonyl-5,5-dimethyl-thiazolidine-4-carbonyl)-amino]-3-(3-phenethyl-ureido)-propionic acid, or 2-[(3-Benzenesulfonyl-5,5-dimethyl-thiazolidine-4-carbonyl)-amino]-3-[3-(2,2-diphenyl-ethyl)-ureido]-propionic acid.

In certain other embodiments, $R^7$ may be phenyl substituted with one or more alkyl, halo, trifluoromethyl, or trifluoromethoxy. Exemplary compounds of such embodiments include
2-[(3-Benzenesulfonyl-5,5-dimethyl-thiazolidine-4-carbonyl)-amino]-3-[3-(2-methyl-benzyl)-ureido]-propionic acid;
2-[(3-Benzenesulfonyl-5,5-dimethyl-thiazolidine-4-carbonyl)-amino]-3-[3-(3-methyl-benzyl)-ureido]-propionic acid;
2-[(3-Benzenesulfonyl-5,5-dimethyl-thiazolidine-4-carbonyl)-amino]-3-[3-(4-methyl-benzyl)-ureido]-propionic acid;
2-[(3-Benzenesulfonyl-5,5-dimethyl-thiazolidine-4-carbonyl)-amino]-3-[3-(2,6-difluoro-benzyl)-ureido]-propionic acid;
2-[(3-Benzenesulfonyl-5,5-dimethyl-thiazolidine-4-carbonyl)-amino]-3-[3-(3,5-difluoro-benzyl)-ureido]-propionic acid;
2-[(3-Benzenesulfonyl-5,5-dimethyl-thiazolidine-4-carbonyl)-amino]-3-[3-(4-fluoro-benzyl)-ureido]-propionic acid;
2-[(3-Benzenesulfonyl-5,5-dimethyl-thiazolidine-4-carbonyl)-amino]-3-[3-(4-chloro-benzyl)-ureido]-propionic acid;
2-[(3-Benzenesulfonyl-5,5-dimethyl-thiazolidine-4-carbonyl)-amino]-3-[3-(4-bromo-benzyl)-ureido]-propionic acid;
2-[(3-Benzenesulfonyl-5,5-dimethyl-thiazolidine-4-carbonyl)-amino]-3-[3-(4-trifluoromethoxy-benzyl)-ureido]-propionic acid; and
2-[(3-Benzenesulfonyl-5,5-dimethyl-thiazolidine-4-carbonyl)-amino]-3-[3-(4-trifluoromethyl-benzyl)-ureido]-propionic acid.

In certain embodiments wherein $R^4$ and $R^5$ are each —$CH_3$, X is S, and $R^0$ is —$CH_2$—, $R^6$ may be —$CH_3$ and $R^7$ may be phenyl. An example of a compound in accordance with such embodiments is 2-[(3-Benzenesulfonyl-5,5-dimethyl-thiazolidine-4-carbonyl)-amino]-3-[3-(1-phenyl-ethyl)-ureido]-propionic acid.

In other aspects of the present invention, $R^6$ is —H, $R^7$ is phenyl, and X is S or O. In some embodiments, $R^4$ and $R^5$ are both H or are both —$CH_3$. Exemplary compounds of such embodiments include 2-[(3-Benzenesulfonyl-thiazolidine-4-carbonyl)-amino]-3-(3-benzyl-ureido)-propionic acid, and 2-[(3-Benzenesulfonyl-oxazolidine-4-carbonyl)-amino]-3-(3-benzyl-ureido)-propionic acid. In other embodiments, one of $R^4$ and $R^5$ is H, and the other of $R^4$ and $R^5$ is —$CH_3$. For example, the compound may be 2-[(3-Benzenesulfonyl-5-methyl-oxazolidine-4-carbonyl)-amino]-3-(3-benzyl-ureido)-propionic acid.

In yet other embodiments of the present invention, X may be a bond. In such instances, $R^6$ may be H, and $R^7$ may be aryl or aralkyl. An exemplary compound is 2-[(1-Benzenesulfonyl-azetidine-2-carbonyl)-amino]-3-(3-benzyl-ureido)-propionic acid.

In another aspects, the present invention is directed to methods for treating at least one α2β1-affected disease state or infection comprising administering to a subject in need thereof a composition comprising a therapeutically effective amount of a compound having the formula I, as described above. The present methods are intended to embrace the administration of a therapeutically effective amount of any compound or compounds disclosed herein. The composition may additionally comprise a pharmaceutically acceptable carrier, diluent, or excipient. Additionally or alternatively, the composition may comprise a stereochemically enriched mixture of compounds of the formula I.

In accordance with the present methods, subject may be suffering from or susceptible to one or more of acute coronary syndromes, stroke, ischaemic complications of peripheral vascular disease, deep vein thrombosis (DVT), myocardial infarction, coronary artery disease, cerebrovascular disease, peripheral arterial disease, diabetes mellitus, atrial fibrillation, congestive heart failure, pulmonary embolism, and other vascular-related disorders that will be readily appreciated by those skilled in the art. The subject may also or alternatively be suffering from or susceptible to one or more of human melanoma, hepatocellular carcinoma, breast cancer, lung cancer, ovarian cancer, and other cancers or cancer-related disorders. Likewise, the subject may be suffering from or susceptible to one or more of rheumatoid arthritis, diabetic retinopathy, and other rheumatoid- or diabetes-related disorders.

The disease state or infection may be matrix reorganization-affected, angiogenesis-affected, cell migration-, cell proliferation-, cell colonization-, or metastasis-affected, leukocyte infiltration-affected, edema-affected, or any combination thereof. In a preferred embodiment, the disease state or infection is angiogenesis-affected.

In other embodiments, subject may be suffering from or susceptible to viral infection. The viral infection may be at least partially attributable to human cytomegalovirus (HCMV), rotaviruses, Piconaviridae viruses, or related viruses.

The compounds employed in the present invention may exist in prodrug form. As used herein, "prodrug" is intended to include any covalently bonded carriers which release the active parent drug, for example, as according to the formulas or compounds employed in the methods of the present invention in vivo when such prodrug is administered to a subject. Since prodrugs are known to enhance numerous desirable qualities of pharmaceuticals (e.g., solubility, bioavailability, manufacturing, etc.) the compounds of the present invention may, if desired, be delivered in prodrug form. Thus, the present invention contemplates methods of delivering prodrugs. Prodrugs of the compounds employed in the present invention, for example, according to formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

In a further aspect, the invention relates to a pharmaceutical composition comprising a compound of formula I and a pharmaceutically acceptable carrier, diluent, or excipient. The applicable carrier, diluent, or excipient may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

The compounds of the invention may be administered in an effective amount by any of the conventional techniques well-established in the medical field. The compounds employed in the methods of the present invention including, for example, the compounds of formula I may be administered by any means that results in the contact of the active agents with the agents' site or sites of action in the body of a patient. The compounds may be administered by any conventional means available.

Preferably the pharmaceutical composition is in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein one active ingredient is compressed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The dose may also be provided by controlled release of the compound, by techniques well known to those in the art.

The compounds useful in the methods of the present invention may be prepared in a number of ways well known to those skilled in the art. The compounds can be synthesized, for example, by the methods as described below, or variations thereon as appreciated by the skilled artisan. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, or commercial industrial scale.

The present invention is further defined in the following Examples. It should be understood that these examples, while indicating preferred embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Molecular Synthesis

The thiazolidyl-diaminopropionic acid derivatives were synthesized by the solid phase route illustrated in Scheme 1. Fmoc-Dap(Aloc)-OH was attached to bromomethyl Wang resin using CsI as the catalyst (1). The Fmoc group was deprotected using standard methodology of 20% piperidine in DMF before Fmoc-protected L-5,5-dimethylthiazolidine carboxylic acid was appended under standard peptide coupling conditions (2). Deprotection of the Fmoc group was then followed by sulfonamide formation through reaction of the thiazolidine with benzylsulfonyl chloride (3). The orthogonal allyloxycarbonyl (Aloc) protecting group on Dap was removed using Pd(PPh$_3$)$_4$ and PhSiPh$_3$ in degassed methylene chloride under an inert N$_2$ atmosphere. Urea formation of the free amine using freshly synthesized or commercial isocyanates followed by cleavage from the resin gave the desired α2β1 inhibitors 4-22.

Scheme 1

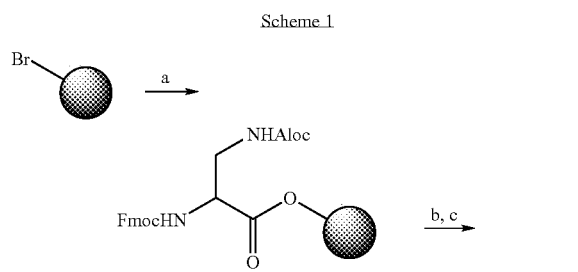

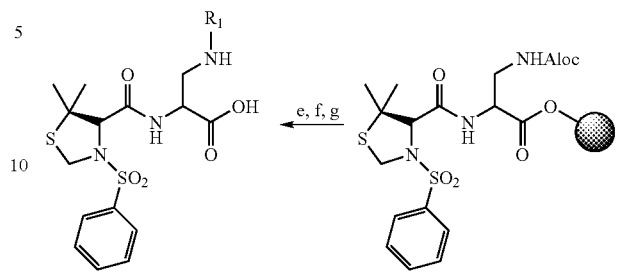

Reagents and conditions for Scheme 1 were as follows: (a) Fmoc-Dap(Aloc)-OH, CsI, DIEA, DMF; (b) 20% piperidine in DMF; (c) (S)-3-Fmoc-5,5-dimethylthiazolidine-4-carboxylic acid (2), HATU, HOBt, DIEA, DMF; (d) PhSO$_2$Cl, DIEA, DCM; (e) Pd(PPh$_3$)$_4$, PhSiH$_3$, DCM; (f) R$_1$—NCO, DIEA, DMF; (g) TFA.

In other embodiments, compounds in accordance with the present invention were prepared in accordance with synthesis Scheme 2:

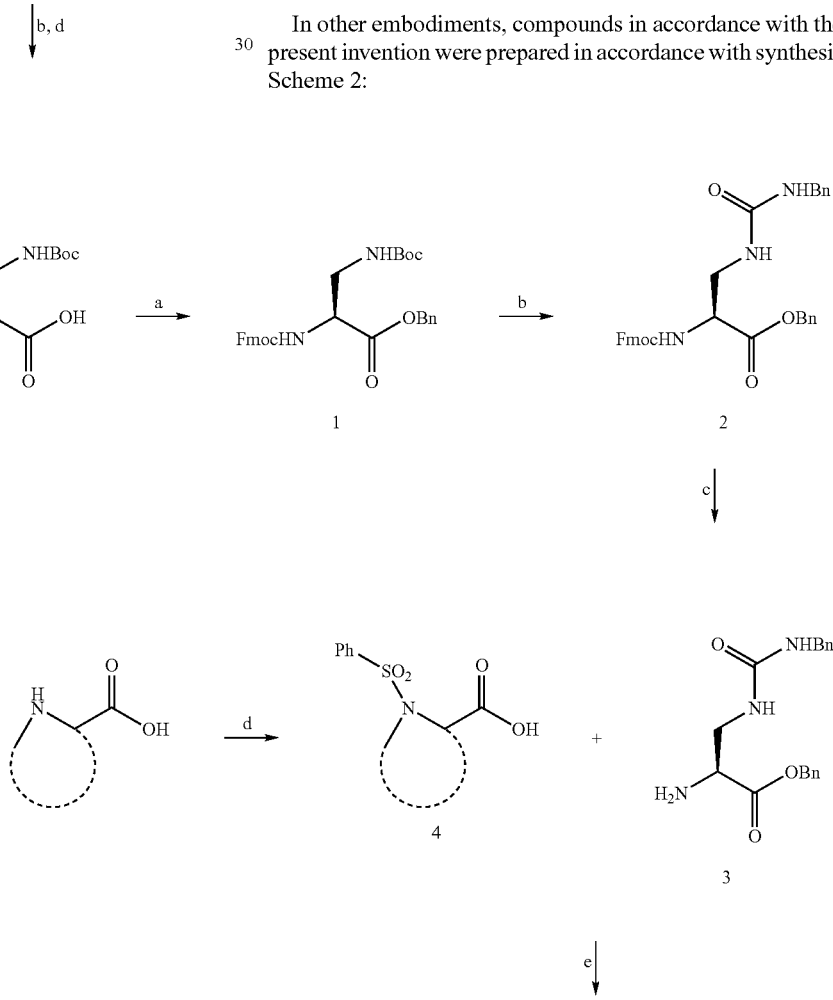

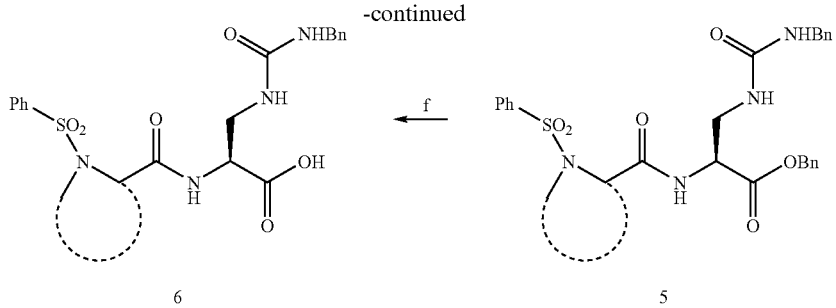

Reagents and conditions for Scheme 2 were as follows: (a) BnBr, NaHCO₃, DMF; (b) (i) TFA, CH₂Cl₂; (ii) i-Pr₂EtN, BnNCO, DMF; (c) Et₂NH, CH₂Cl₂; (d) PhSO₂Cl, NaHCO₃, DMF/H₂O; (e) HATU, HOAt, i-Pr₂EtN, DMF; (f) for sulfur containing heterocycles: BCl₃, CH₂Cl₂; for oxygen containing heterocycles: Pd/C, H₂, MeOH.

For example, Scheme 2 was used to form 2-[(1-Benzenesulfonyl-azetidine-2-carbonyl)-amino]-3-(3-benzyl-ureido)-propionic acid (found to have an $IC_{50}$ of 215 nM); 2-[(3-Benzenesulfonyl-thiazolidine-4-carbonyl)-amino]-3-(3-benzyl-ureido)-propionic acid (found to have an $IC_{50}$ of 12 nM); 2-[(3-Benzenesulfonyl-5-methyl-oxazolidine-4-carbonyl)-amino]-3-(3-benzyl-ureido)-propionic acid found to have an $IC_{50}$ of 12 nM); and, 2-[(3-Benzenesulfonyl-oxazolidine-4-carbonyl)-amino]-3-(3-benzyl-ureido)-propionic acid (found to have an $IC_{50}$ of 82 nM).

Example 2

Platelet Adhesion Assay

The series of compounds was tested for the ability to block washed human platelet binding to soluble type I collagen. Previously, the inventors generated potent and specific inhibitors of integrin α2β1 based on a benzyl urea scaffold in the orthogonal position diaminopropionic acid scaffold.[22] Subsequent structure-activity relationship studies improved the proline moiety to a pencillamine-derived dimethyl thiazolidine. Further understanding was sought with respect to the SAR of the urea functionality and its spatial positioning. Starting from the benzyl group, a determination was sought as to whether the phenyl had a preferred spatial conformation: interesting, the (R) conformation (7) of the α-methyl benzyl urea displayed >25-fold greater potency than the (S) conformation (8). It was subsequently found that the inhibitors were mostly insensitive to substitutions on the ring in any of the positions (9-11, 13-16). More sterically bulky groups at the para position (17-18) decreased potency. Further increasing the linker length between the NH of the urea and the phenyl ring did not improve efficacy (22). The binding pocket was also found to be intolerant of increasing steric bulk by adding additional phenyl rings to the inhibitor (20-21). Loss of aromaticity in the bulky hydrocarbon group attached to the urea (19, 23) was found to have had a negative effect on potency, but size seemed to play a larger role in inhibitor affinity than aromaticity.

TABLE 1

| | $R_1$ | $IC_{50}$ (nM) |
|---|---|---|
| 5 | O, N-benzyl amide | 9 |
| 6 | S, N-benzyl thioamide | 7 |
| 7 | O, N-(R)-α-methylbenzyl amide | 22 |
| 8 | O, N-(S)-α-methylbenzyl amide | >500 |
| 9 | O, N-(2-methylbenzyl) amide | 4 |
| 10 | O, N-(3-methylbenzyl) amide | 8 |

TABLE 1-continued
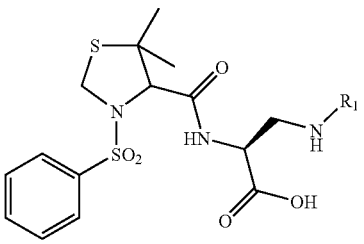
| | R₁ | IC₅₀ (nM) |
|---|---|---|
| 11 | 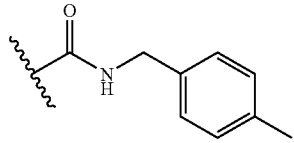 | 6 |
| 12 | 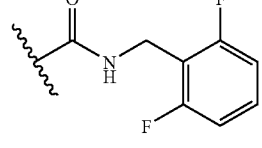 | 39 |
| 13 | 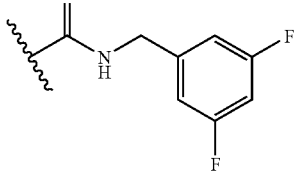 | 9 |
| 15 | 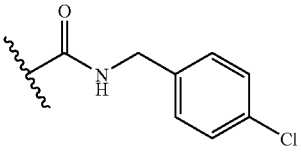 | 6 |
| 16 | 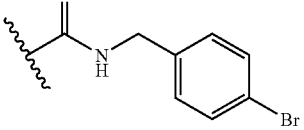 | 4 |
| 17 | 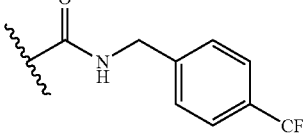 | 41 |
| 18 | 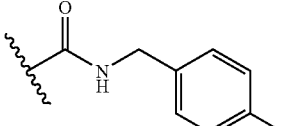 | 13 |
| 19 | 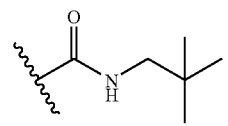 | 15 |
TABLE 1-continued
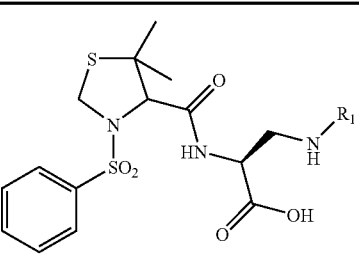
| | R₁ | IC₅₀ (nM) |
|---|---|---|
| 20 | 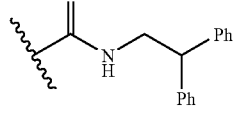 | >2000 |
| 21 | 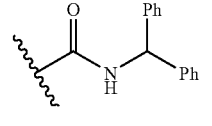 | 320 |
| 22 | 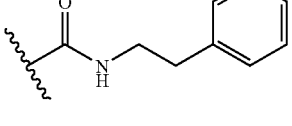 | 133 |
| 23 | 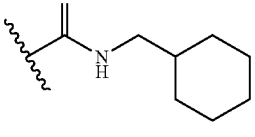 | 28 |
Compounds Produced in Accordance with Scheme 2:
| | | IC₅₀ (nM) |
|---|---|---|
| 24 |  | 215 |
| 25 |  | 12 |

| | | IC$_{50}$ (nM) |
|---|---|---|
| 26 | [structure: phenylsulfonyl-oxazolidine-carbonyl-Dap(benzylureido)-OH] | 82 |
| 27 | [structure: phenylsulfonyl-methyl-oxazolidine-carbonyl-Dap(benzylureido)-OH] | 12 |

To investigate the difference in affinity between compounds 7 and 8, molecular modeling was employed to calculate the quantum mechanical geometries of the molecules (data not shown).

Example 3

Inhibitor Selectivity

Platelets express several integrins, including αIIbβ3, αvβ3, α2β1, α5β1, and α6β1.[23] A study was performed with respect to the ability of some of the most potent compounds of the present invention to block platelet binding to the specific ligands of other platelet integrins to determine the selectivity of our inhibitors. Results are shown below in Table 2:

TABLE 2

| Integrin | Ligand | 5 | 9 | 10 | 15 |
|---|---|---|---|---|---|
| | | IC$_{50}$(nM) | | | |
| A2β1 | Collagen I | 1 | 4 | 8 | 6 |
| A5β1 | Fibronectin | >1000 | >1000 | >1000 | >1000 |
| αvβ3 | Osteopontin | | | | |

The inhibitors demonstrated no effect on integrin α5β1 binding to fibronectin (in the presence of abciximab, the human-murine monoclonal antibody to beta3 integrins including αIIbβ3 and αvβ3 to isolate α5β1 activity)[24] at concentrations inhibitor greater than 1000-fold the IC$_{50}$ of the integrin α2β1-mediated adhesion to type I collagen.

To further examine the selectivity of the inhibitors, the ability of the compounds to inhibit platelet aggregation in response to fibrinogen was investigated. Platelet aggregation is largely mediated through the function of integrin αIIbβ3.[25] The compounds were observed to have no effect on platelet aggregation at concentrations of 20 μM, greater than 20,000-fold the IC$_{50}$ of the integrin α2β1-mediated adhesion to type I collagen.

Example 4

Experimental Details

General. Unless otherwise indicated, all reactions were run under nitrogen gas. Anhydrous solvents were obtained from commercial suppliers. $^1$H-NMR and $^{13}$C-NMR were recorded on a DMX-360 or DRX-500 spectrometer. Chemical shifts are reported relative to an internal DMSO-d$_6$ standard (δ 2.50 for $^1$H and δ 39.52 for $^{13}$C). High-resolution mass spectra were obtained using an Autospec high resolution double focusing electrospray ionization/chemical ionization spectrometer with either DEC 11/73 or OPUS software data system. Preparative HPLC was performed on a Varian HPLC system using a GRACEVYDAC C-18 column, 250×22 mm, 100 Å, and a flow rate of 10 mL/min; λ=220 nm; mobile phase A (0.1% TFA in H$_2$O) and mobile phase B (0.1% TFA in 90% CH$_3$CN/10% H$_2$O). The purified compounds were lyophilized.

General Procedure for the Preparation of Inhibitors. The 4-(bromomethyl)phenoxymethyl polystyrene resin was swelled in DMF (15 mL/g resin). Fmoc-Dap(Aloc)-OH (1.5 eq), CsI (1.5 eq), DIEA (2.0 eq) were added, and the reaction was stirred for 18 hours at 25° C. The resin was filtered and washed repeatedly with DMF and MeOH. After deprotection of the Fmoc group with 20% piperidine in DMF, the resin was repeatedly washed with DMF. The resin was then suspended in DMF and (S)-3-Fmoc-5,5-dimethylthiazolidine-4-carboxylic acid (2.0 eq), HATU (2.0 eq), HOBt (2.0 eq), and DIEA (4.0 eq) were added and the resin was stirred for 18 hours at 25° C. The resin was filtered and washed repeatedly with DMF. The resin was then suspended in DCM and stirred with benzenesulfonyl chloride (3.0 eq) and DIEA (6.0 eq) for 18 hours. The resin was washed repeated with DMF. The resin was washed with degassed DCM for 20 minutes and then Pd(PPh$_3$)$_4$ (0.5 eq) and PhSiH$_3$ (25 eq) were added. The reaction was stirred for 3 hours under N$_2$. The resin was washed repeatedly with DMF and DCM and then dried overnight under a high vacuum. The resin was then suspended in DCM and isocyanate derivatives (10 eq) and DIEA (6 eq) were added and the reaction was stirred for 18 hours at 25° C. The resin was then filtered and washed repeatedly with DCM and DMF. The final products were cleaved from the resin with 100% TFA treatment for 1 hour. The isocyanate derivatives were purchased commercially or prepared from the corresponding free amine by treatment with triphosgene (0.5 eq) and pyridine (6 eq) in DCM for 3 hours at 25° C.

(S)-3-(((9H-fluoren-9-yl)methoxy)carbonyl)-5,5-dimethylthiazolidine-4-carboxylic Acid (2). L-pencillamine (5 g) was dissolved in hot dH$_2$O (50 mL) then cooled to 0° C. 37% formaldehyde in dH$_2$O (5 mL) was added dropwise via syringe and the reaction was allowed to slowly warm to RT while stirring overnight. The solvents were removed by rotary evaporation and the resulting solid residue was used directly. The residue was dissolved in dH$_2$O (30 mL). FmocOSu (6.5 g) was dissolved in acetone (30 mL) and the solution was added to the amine via syringe at RT and stirred overnight. The acetone was removed by rotary evaporation and the remaining aqueous solution was acidified to pH=2 with 1.0 M HCl. The aqueous solution was extracted with ethyl acetate (3×) and CHCl$_3$ (3×), the combined organics were washed with dH$_2$O, dried over MgSO$_4$, and concentrated by rotary evaporation to yield 2 as an off-white foam (69% yield). $^1$H NMR (360 MHz, DMSO-d$_6$): δ 1.41 (d, J=15.1 Hz, 3H), 1.53 (d, J=8.9 Hz, 3H), 4.01 (q, J=J=J=7.1 Hz, 1H), 4.17-4.33 (m, 2H), 4.35-4.39 (m, 2H), 4.57-4.60 (m, 1H), 7.30-7.37 (m, 2H), 7.42 (t, J=J=7.4 Hz, 2H), 7.62-7.68 (m, 2H), 7.89 (t, J=J=6.9 Hz, 2H), 13.03 (s, 1H); $^{13}$C NMR (90 MHz, DMSO-d$_6$): δ 24.63, 30.12, 46.57, 51.79, 59.74, 67.16, 71.16, 125.23, 127.19, 127.73, 140.74, 143.57, 153.73, 170.19

2-[1-Benzenesulfonylamino-5,5-dimethylthiazolidine-4-carbonyl]-amino]-3-[3-benzylureido]-propionic acid (5). $^1$H NMR (500 MHz, DMSO-d$_6$): δ 1.20 (s, 3H), 1.28 (s, 3H), 3.32-3.38 (m, 1H), 3.42-3.47 (m, 1H), 4.40 (s, 1H), 4.15-4.22 (m, 3H), 4.63 (dt, J=8.9 Hz, J=9.4 Hz, 2H), 6.07 (br, 1H), 6.66 (br, 1H), 7.19-7.25 (m, 3H), 7.30 (dd, J=J=7.5 Hz, 2H), 7.63 (dd, J=J=7.8 Hz, 2H), 7.72 (t, J=J=7.4 Hz, 1H), 7.88 (d, J=7.4 Hz, 2H), 8.45 (d, J=7.0 Hz, 1H); $^{13}$C NMR (125 MHz, DMSO-$d_6$): δ 24.60, 29.44, 40.68, 42.97, 50.39, 53.48, 54.61, 72.38, 126.56, 127.06, 127.60, 128.18, 129.35, 133.55, 136.60, 140.56, 158.31, 167.57, 171.69; EI-MS: m/z (M+H$^+$): 521.1530 (calcd), 521.1530 (found).

2-[1-Benzenesulfonylamino-5,5-dimethylthiazolidine-4-carbonyl]-amino]-3-[3-benzylthioureido]-propionic acid (6). $^{13}$C NMR (90 MHz, DMSO-$d_6$): δ 20.66, 24.41, 29.55, 40.66, 42.70, 50.29, 53.42, 54.39, 72.37, 127.05, 127.58, 127.98, 128.71, 129.32, 133.51, 135.53, 136.63, 137.45, 158.20, 167.18, 171.27

2-[1-Benzenesulfonylamino-5,5-dimethylthiazolidine-4-carbonyl]-amino]-3-[1-((R)-1-phenethyl)ureido]-propionic acid (7). $^1$H NMR (360 MHz, DMSO-$d_6$): δ 1.17 (s, 3H), 1.26 (s, 3H), 1.31 (d, J=6.9 Hz, 3H), 3.14-3.42 (m, 2H), 4.01 (s, 1H), 4.06-4.15 (m, 1H), 4.64 (dd, J=9.6 Hz, J=5.0 Hz, 2H), 4.75 (t, J=J=7.2 Hz, 1H), 5.83-5.93 (m, 1H), 6.42 (d, J=11.3 Hz, 1H), 7.10-7.12 (m, 1H), 7.22-7.32 (m, 3H), 7.65 (t, J=J=7.8 Hz, 2H), 7.71 (d, J=7.3 Hz, 1H), 7.88 (d, J=7.3 Hz, 2H), 8.42 (d, J=7.0 Hz, 1H); $^{13}$C NMR (90 MHz, DMSO-$d_6$): δ 23.21, 24.59, 29.41, 40.46, 48.62, 50.38, 53.75, 54.59, 72.36, 125.79, 126.40, 127.57, 128.14, 129.32, 133.52, 136.54, 145.46, 157.47, 167.53, 171.64; EI-MS: m/z (M+Na$^+$): 557.1504 (calcd), 557.1516 (found).

2-[1-Benzenesulfonylamino-5,5-dimethylthiazolidine-4-carbonyl]-amino]-3-[1-((S)-1-phenethyl)ureido]-propionic acid (8). $^1$H NMR (360 MHz, DMSO-$d_6$): δ 1.20 (s, 3H), 1.26 (s, 3H), 1.31 (d, J=10 Hz, 3H), 3.26-3.31 (m, 2H), 4.04 (s, 1H), 4.15 (q, J=J=5 Hz, 2H), 4.60 (dd, J=5 Hz, J=9 Hz, 2H), 4.75 (t, J=J=5 Hz, 1H), 5.91 (br, 1H), 6.63 (br, 1H), 7.17-7.22 (m, 1H), 7.27-7.31 (m, 3H), 7.62 (t, J=J=5 Hz, 2H), 7.72 (t, J=J=10 Hz, 1H), 7.88 (d, J=10 Hz, 2H), 8.41 (d, J=5 Hz, 1H); $^{13}$C NMR (125 MHz, DMSO-$d_6$): δ 23.19, 24.55, 29.46, 40.62, 48.55, 50.34, 53.46, 54.58, 72.39, 125.79, 126.42, 127.59, 128.16, 129.30, 133.48, 136.70, 145.48, 157.56, 167.62, 171.63

2-[1-Benzenesulfonylamino-5,5-dimethylthiazolidine-4-carbonyl]-amino]-3-[3-(2-methylbenzyl)ureido]-propionic acid (9). $^1$H NMR (360 MHz, DMSO-$d_6$): δ 1.20 (s, 3H), 1.29 (s, 3H), 2.25 (s, 3H), 3.29-3.37 (m, 1H), 3.37-3.46 (m, 1H), 4.03 (s, 1H), 4.18 (s, 3H), 4.63 (dd, J=9.5 Hz, J=5.5 Hz, 2H), 6.04 (br, 1H), 6.53 (br, 1H), 7.11 (d, J=6.0 Hz, 2H), 7.19-7.22 (m, 1H), 7.63 (t, J=J=7.2 Hz, 2H), 7.72 (t, J=J=7.4 Hz, 1H), 7.88 (d, J=7.3 Hz, 2H), 8.44 (d, J=7.0 Hz, 1H); $^{13}$C NMR (90 MHz, DMSO-$d_6$): δ 18.50, 24.57, 29.43, 40.20, 50.34, 53.44, 54.57, 72.33, 125.65, 126.60, 127.55, 129.29, 129.76, 133.49, 135.35, 136.59, 137.99, 158.17, 167.52, 171.63; EI-MS: m/z (M+Na$^+$): 557.1504 (calcd), 557.1525 (found).

2-[1-Benzenesulfonylamino-5,5-dimethylthiazolidine-4-carbonyl]-amino]-3-[3-(3-methylbenzyl)ureido]-propionic acid (10). $^1$H NMR (360 MHz, DMSO-$d_6$): δ 1.20 (s, 3H), 1.28 (s, 3H), 2.27 (s, 3H), 3.29-3.37 (m, 1H), 3.37-3.46 (m, 1H), 4.04 (s, 1H), 4.20 (br, 2H), 4.63 (dd, J=9.5 Hz, J=4.5 Hz, 2H), 6.05 (br, 1H), 6.62 (br, 1H), 7.01-7.05 (m, 2H), 7.17 (t, J=J=7.4 Hz, 1H), 7.63 (t, J=J=7.3 Hz, 2H), 7.72 (t, J=J=7.3 Hz, 1H), 7.88 (d, J=7.3 Hz, 2H), 8.45 (d, J=7.0 Hz, 1H); $^{13}$C NMR (90 MHz, DMSO-$d_6$): δ 20.98, 24.59, 29.45, 40.67, 42.95, 50.37, 53.48, 54.59, 72.36, 124.18, 127.18, 127.59, 127.67, 128.08, 129.33, 133.52, 136.61, 137.21, 140.40, 158.28, 167.55, 171.66

2-[1-Benzenesulfonylamino-5,5-dimethylthiazolidine-4-carbonyl]-amino]-3-[3-(4-methylbenzyl)ureido]-propionic acid (11). $^1$H NMR (360 MHz, DMSO-$d_6$): δ 1.20 (s, 3H), 1.28 (s, 3H), 2.26 (s, 3H), 3.31-3.38 (m, 1H), 3.38-3.47 (m, 1H), 4.40 (s, 1H), 4.19 (br, 3H), 4.63 (dd, J=9.3 Hz, J=4.1 Hz, 2H), 6.04 (br, 1H), 6.60 (br, 1H), 7.11 (dd, J=8.1 Hz, J=5.8 Hz, 2H), 7.63 (t, J=J=7.1 Hz, 2H), 7.72 (t, J=J=7.2 Hz, 1H), 7.88 (d, J=7.2 Hz, 2H), 8.45 (d, J=7.0 Hz, 1H); $^{13}$C NMR (90 MHz, DMSO-$d_6$): δ 20.61, 24.57, 29.43, 40.65, 42.72, 50.35, 53.48, 54.58, 72.35, 127.04, 127.57, 128.70, 129.31, 133.50, 135.21, 136.61, 137.43, 158.27, 167.53, 171.63; EI-MS: m/z (M+Na$^+$): 557.1504 (calcd), 557.1476 (found).

2-[1-Benzenesulfonylamino-5,5-dimethylthiazolidine-4-carbonyl]-amino]-3-[3-(3,5-difluorobenzyl)ureido]-propionic acid (12). $^1$H NMR (360 MHz, DMSO-$d_6$): δ 1.18 (s, 3H), 1.27 (s, 3H), 3.31-3.48 (m, 1H), 4.03 (s, 2H), 4.20 (d, J=6.0 Hz, 1H), 4.23 (d, J=5.4 Hz, 2H), 4.62 (dd, J=9.5 Hz, J=5.1 Hz, 2H), 6.15 (br, 1H), 6.77 (br, 1H), 6.94 (d, J=6.7 Hz, 2H), 7.03 (t, J=J=9.8 Hz, 1H), 7.63 (t, J=J=7.8 Hz, 2H), 7.72 (t, J=J=7.3 Hz, 1H), 7.87 (d, J=7.2 Hz, 2H), 8.42 (d, J=7.1 Hz, 1H); $^{13}$C NMR (90 MHz, DMSO-$d_6$): δ 24.58, 29.38, 40.70, 42.24, 50.37, 53.30, 54.55, 72.38, 101.53 (t, J=J=102.6 Hz), 109.62 (d, J=71.3 Hz), 127.59, 129.33, 133.53, 136.57, 145.78 (t, J=J=34.2 Hz), 158.22, 160.89 (d, J=52.7 Hz), 163.60 (d, J=52.2 Hz), 167.58, 171.63; EI-MS: m/z (M+Na$^+$): 579.1160 (calcd), 579.1160 (found).

2-[1-Benzenesulfonylamino-5,5-dimethylthiazolidine-4-carbonyl]-amino]-3-[3-(2,6-difluorobenzyl)ureido]-propionic acid (13). $^1$H NMR (360 MHz, DMSO-$d_6$): δ 1.19 (s, 3H), 1.24 (s, 3H), 3.29-3.43 (m, 2H), 4.03 (s, 1H), 4.09 (t, J=J=6.8 Hz, J=5.8 Hz, 1H), 4.27 (d, J=4.2 Hz, 2H), 4.59 (t, J=J=9.4 Hz, J=5.3 Hz, 2H), 5.97 (br t, J=J=5.5 Hz, 1H), 6.61 (br, 1H), 7.03 (t, J=J=8.0 Hz, 2H), 7.34 (m, 1H), 7.60 (t, J=7.8 Hz, 2H), 7.69 (t, J=7.4 Hz, 1H), 7.86 (d, J=7.1 Hz, 2H), 8.39 (d, 7.0 Hz, 1H); $^{13}$C NMR (90 MHz, DMSO-$d_6$): δ 24.48, 29.49, 31.14, 40.56, 50.33, 53.44, 54.57, 72.32, 111.32 (d, J=100.1 Hz), 114.96 (t, J=J=76.7 Hz), 127.57, 129.31, 129.51 (t, J=J=41.4 Hz), 133.50, 136.61, 157.81, 159.50 (d, J=34.2 Hz), 162.23 (d, J=33.8 Hz), 167.56, 171.61; EI-MS: m/z (M+H$^+$): 557.1340 (calcd), 557.1349 (found).

2-[1-Benzenesulfonylamino-5,5-dimethylthiazolidine-4-carbonyl]-amino]-3-[3-(4-fluorobenzyl)ureido]-propionic acid (14). $^1$H NMR (360 MHz, DMSO-$d_6$): δ 1.20 (s, 3H), 1.28 (s, 3H), 3.34-3.46 (m, 2H), 4.04 (s, 1H), 4.15-4.19 (m, 3H), 4.63 (dd, J=9.5 Hz, J=4.5 Hz, 2H), 6.06 (br, 1H), 6.67 (br, 1H), 7.11 (t, J=J=8.9 Hz, 2H), 7.28 (t, J=J=5.7 Hz, 2H), 7.63 (t, J=J=7.3 Hz, 2H), 7.72 (t, J=J=7.4 Hz, 1H), 7.88 (d, J=7.2 Hz, 2H), 8.43 (d, J=7.0 Hz, 1H); $^{13}$C NMR (90 MHz, DMSO-$d_6$): δ 24.56, 29.40, 40.66, 42.22, 50.36, 53.41, 54.57, 72.36, 114.71, 114.94, 127.58, 128.90, 128.99, 129.32, 133.52, 136.59, 136.78, 136.81, 158.25, 159.68, 162.35, 167.56, 171.64; EI-MS: m/z (M+Na$^+$): 561.1254 (calcd), 561.1264 (found).

2-[1-Benzenesulfonylamino-5,5-dimethylthiazolidine-4-carbonyl]-amino]-3-[3-(4-chlorobenzyl)ureido]-propionic acid (15). $^1$H NMR (500 MHz, DMSO-$d_6$): δ 1.20 (s, 3H), 1.29 (s, 3H), 4.04 (s, 2H), 4.17-4.21 (m, 4H), 4.63 (dd, J=13.2 Hz, J=8.0 Hz, 2H), 6.12 (br, 1H), 6.72 (br, 1H), 7.29 (d, J=11.8 Hz, 2H), 7.35 (d, J=9.1 Hz, 2H), 7.65 (t, J=J=10.0 Hz, 2H), 7.73 (t, J=J=10.3 Hz, 2H), 7.89 (d, J=10.0 Hz, 2H), 8.45 (d, J=9.8 Hz, 1H); $^{13}$C NMR (125 MHz, DMSO-$d_6$): δ 25.01, 29.81, 41.12, 42.72, 50.82, 53.86, 55.02, 72.85, 128.04, 128.53, 129.32, 129.80, 131.49, 134.01, 137.00, 140.18, 158.76, 168.08, 172.09; EI-MS: m/z (M+Na$^+$): 577.0958 (calcd), 577.0969 (found).

2-[1-Benzenesulfonylamino-5,5-dimethylthiazolidine-4-carbonyl]-amino]-3-[3-(4-bromobenzyl)ureido]-propionic acid (16). $^1$H NMR (360 MHz, DMSO-$d_6$): δ 1.19 (s, 3H), 1.27 (s, 3H), 3.32-3.35 (m, 1H), 3.36-3.46 (m, 1H), 4.04 (s, 2H), 4.15-4.21 (m, 4H), 4.62 (dd, J=9.5 Hz, J=4.7 Hz, 2H), 6.10 (br, 1H), 6.70 (br, 1H), 7.20 (d, J=8.4 Hz, 2H), 7.47 (d, J=8.4 Hz, 2H), 7.63 (t, J=J=7.2 Hz, 2H), 7.72 (t, J=J=7.4 Hz, 1H), 7.88 (d, J=7.2 Hz, 2H), 8.43 (d, J=7.0 Hz, 1H); $^{13}$C NMR (90 MHz, DMSO-$d_6$): δ 24.58, 29.41, 40.68, 42.32, 50.37, 53.89, 54.58, 72.37, 119.47, 127.59, 129.25, 130.99, 133.53, 136.60, 140.21, 158.26, 167.58, 171.65; EI-MS: m/z (M+Na$^+$): 621.0453 (calcd), 621.0464 (found).

2-[1-Benzenesulfonylamino-5,5-dimethylthiazolidine-4-carbonyl]-amino-3-[3-(4-trifluoromethylbenzyl)ureido]-propionic acid (17). $^1$H NMR (360 MHz, DMSO-$d_6$): δ 1.19 (s, 3H), 1.45 (s, 3H), 3.33-3.37 (m, 1H), 3.37-3.47 (m, 1H), 4.02 (s, 1H), 4.21 (t, J=J=6.8 Hz, 1H), 4.30 (s, 2H), 4.59-4.66 (m, 2H), 6.15 (br, 1H), 6.79 (br, 1H), 7.46 (d, J=7.7 Hz, 2H), 7.61-7.66 (m, 4H), 7.71 (d, J=7.2 Hz, 1H), 7.89 (d, J=7.1 Hz, 2H), 8.43 (d, J=6.9 Hz, 1H); $^{13}$C NMR (90 MHz, DMSO-$d_6$): δ 24.57, 29.37, 40.20, 42.54, 50.36, 53.32, 54.56, 72.36, 125.02, 127.58, 129.31, 133.51, 136.58, 145.74, 158.26, 167.57, 171.65; EI-MS: m/z (M$^-$): 587.1246 (calcd), 587.1255 (found).

2-[1-Benzenesulfonylamino-5,5-dimethylthiazolidine-4-carbonyl]-amino-3-[3-(4-trifluoromethoxybenzyl)ureido]-propionic acid (18). $^1$H NMR (360 MHz, DMSO-$d_6$): δ 1.19 (s, 3H), 1.27 (s, 3H), 3.29-3.37 (m, 1H), 3.37-3.47 (m, 1H), 4.04 (s, 1H), 4.16-4.29 (m, 3H), 4.63 (dd, J=9.4 Hz, J=5.2 Hz, 2H), 6.11 (br, 1H), 6.74 (br, 1H), 7.28 (d, J=7.9 Hz, 2H), 7.37 (d, J=8.5 Hz, 2H), 7.63 (t, J=J=7.1 Hz, 2H), 7.72 (d, J=7.2 Hz, 1H), 7.89 (d, J=7.1 Hz, 2H), 8.44 (d, J=6.9 Hz); $^{13}$C NMR (90 MHz, DMSO-$d_6$): δ 24.57, 29.39, 40.68, 42.22, 50.36, 53.37, 54.56, 72.36, 120.78, 127.58, 128.78, 129.32, 133.51, 136.60, 140.28, 146.98, 158.25, 167.57, 171.65

2-[1-Benzenesulfonylamino-5,5-dimethylthiazolidine-4-carbonyl]-amino-3-[3-neopentylureido]-propionic acid (19). $^1$H NMR (360 MHz, DMSO-$d_6$): δ

2-[1-Benzenesulfonylamino-5,5-dimethylthiazolidine-4-carbonyl]-amino-3-[3-(2,2-diphenylethyl)ureido]-propionic acid (20). $^1$H NMR (360 MHz, DMSO-$d_6$): δ 1.19 (s, 3H), 1.26 (s, 3H), 3.30-3.36 (m, 2H), 3.66 (t, J=J=7.3 Hz, 2H), 4.02 (s, 1H), 4.11 (t, J=J=7.5 Hz, 2H), 4.64 (dd, J=9.5 Hz, J=3.4 Hz, 2H), 6.09 (br, 2H), 7.20 (q, J=J=4.2 Hz, 2H), 7.62 (t, J=J=7.4 Hz, 2H), 7.72 (t, J=J=7.5 Hz, 1H), 7.88 (d, J=7.4 Hz, 2H), 8.44 (d, J=6.9 Hz, 1H); EI-MS: m/z (M+Na$^+$): 609.1842 (calcd), 609.1862 (found).

2-[1-Benzenesulfonylamino-5,5-dimethylthiazolidine-4-carbonyl]-amino-3-[3-benzhydrylureido]-propionic acid (21). $^1$H NMR (360 MHz, DMSO-$d_6$): δ EI-MS: m/z (M+Na$^+$): 619.1661 (calcd), 619.1686 (found).

2-[1-Benzenesulfonylamino-5,5-dimethylthiazolidine-4-carbonyl]-amino-3-[1-(phenethyl)ureido]-propionic acid (22). $^1$H NMR (360 MHz, DMSO-$d_6$): δ 1.20 (s, 3H), 1.29 (s, 3H), 2.68 (t, J=J=7.1 Hz, 2H), 3.22 (br, 2H), 3.29-3.44 (m, 2H), 3.75 (br, 4H), 4.03 (s, 1H), 4.14 (q, J=J=J=6.7 Hz, 1H), 4.64 (dd, J=9.5 Hz, J=6.6 Hz, 2H), 6.04 (br, 1H), 6.18 (br, 1H), 7.19 (d, J=7.2 Hz, 2H), 7.27 (d, J=6.7 Hz, 2H), 7.63 (t, J=J=7.3 Hz, 2H), 7.72 (t, J=7.4 Hz, 1H), 7.89 (d, J=7.3 Hz, 2H), 8.45 (d, J=6.9 Hz, 1H); $^{13}$C NMR (90 MHz, DMSO-$d_6$): δ 24.58, 29.43, 36.02, 40.58, 41.05, 50.36, 53.62, 54.60, 72.39, 125.95, 127.59, 128.27, 128.60, 129.32, 133.52, 136.60, 139.62, 158.31, 167.54, 171.62; EI-MS: m/z (M+Na$^+$): 557.1504 (calcd), 557.1497 (found).

2-[1-Benzenesulfonylamino-5,5-dimethylthiazolidine-4-carbonyl]-amino-3-[1-(cyclohexylmethyl)ureido]-propionic acid (23). $^1$H NMR (360 MHz, DMSO-$d_6$): δ 0.784 (m, 2H), 0.97 (m, 3H), 1.20 (s, 3H), 1.28 (s, 3H), 1.93 (br d, J=9.5 Hz, 5H), 2.82 (br d, J=6.4 Hz, 2H), 3.32 (m, 2H), 4.02 (s, 1H), 4.09 (q, J=J=6.9 Hz, 1H), 4.60 (dd, J=9.5 Hz, J=3.7 Hz, 2H), 5.91 (br, 1H), 6.17 (br, 1H), 7.61 (t, J=7.3 Hz, 2H), 7.71 (t, J=J=7.4 Hz, 1H), 8.43 (d, J=6.9 Hz, 1H); $^{13}$C NMR (90 MHz, DMSO-$d_6$): δ 24.59, 25.38, 26.05, 29.44, 30.35, 37.98, 40.21, 45.70, 50.37, 53.70, 54.60, 72.40, 127.59, 129.31, 133.52, 136.59, 158.46, 167.53, 171.63; EI-MS: m/z (M+H$^+$): 527.1998 (calcd), 527.1998 (found).

Preparation of Washed Platelets. All Studies were Conducted Following IRB-approved protocols at the University of Pennsylvania. Human blood was obtained by venipuncture from healthy volunteers using 0.3% sodium citrate as anticoagulant, then acid-citrate-dextrose was added (1 mL per 10 mL blood). Platelet-rich plasma (PRP) was then prepared by centrifugation at 200 g for 20 min. Platelets were obtained from the PRP by addition of prostacyclin (PG I$_2$: 0.1 μg/ml) followed by centrifugation at 1000 g for 10 min. The pelleted platelets were resuspended in HEPES/Tyrode's buffer (20 mM HEPES, 129 mM NaCl, 0.34 mM Na$_2$HPO$_4$, 2.9 mM KCl, 12 mM NaHCO$_3$, 5 mM glucose, 1 mm MgCl$_2$, pH 7.3) and repelleted by repeated PG I$_2$ addition and centrifugation. The platelets were resuspended in GFP buffer (4 mM HEPES, 135 mM NaCl, 2.7 mM KCl, 3.3 mM Na$_2$HPO$_4$, 0.35% BSA, 0.1% glucose, 2 mM MgCl$_2$, pH 7.4) to a final concentration of 2×10$^8$ platelets/mL.[26]

Platelet Adhesion Assays. Immulon 2 flat bottom 96-well Plates (Dynatech Labs, Burlington, Mass.) were coated with soluble type I collagen, fibronectin (FN) or osteopontin (OPN) (5 μg/ml) in PBS for 48 hrs at 4° C. The plates were then washed and blocked with BSA (5 mg/ml in PBS) for at least 24 hr. Adhesion assays using type I collagen contained test compound and 1.6×10$^7$ Platelets in GFP buffer in a final volume of 100 μl. The plates were then incubated for 30 min at 37° C. and washed with TBS (10 mM Tris, 150 mM NaCl, pH 7.4). Quantification of adherent platelets was performed as previously described.[27] Briefly, the platelets were stained for acid phosphatase by adding 0.1 M sodium citrate (pH 5.4) with 0.1% Triton X-100 containing 5 mM p-nitrophenyl phosphate substrate (100 μl/well) and incubated for 40 min at 37° C. Color was then developed by the addition of 50 μl 2.0 M NaOH per well and the plates were read at 405 nm in a Molecular Devices Spectra Max M5 microplate reader. Adhesion to FN- and OPN-coated plates were performed similarly using a modified GFP buffer for resuspension (4 mM HEPES, 147 mM NaCl, 2.7 mM KCl, 0.35% BSA, 0.1% glucose, 1 mM MgCl$_2$, 1 mM MnCl$_2$, pH 7.4). Platelets were stimulated in OPN binding by addition of 20 μM ADP during incubation.[28] The platelets in αvβ3-mediated binding to FN were pretreated with 2 μg per mL ReoPro (abciximab, chimeric 7E3 Fab; Centocor, Malvern Pa.) for 20 minutes at RT.

Platelet Aggregation Assays. Turbidometric measurements of platelet aggregation were performed in a Chrono-Log Lumi-Dual Aggregometer by the method previously described.[29] Aliquots (0.4 mL) of the washed platelets were placed in siliconized cuvettes and stirred at 1000 rpm at 37° C. Aggregation was measured by the increase in light transmission as platelet aggregates formed. The platelets were supplemented with 200 μg/ml human fibrinogen (Enzyme Research Laboratories) and 1 mM CaCl$_2$ prior to adding test compounds. The compounds (in DMSO) were added to achieve final concentrations ranging from 200 nM to 20 μM and compared to DMSO controls. All samples had 0.5% DMSO total.

1. Saelman, E. U. M. N., H. K.; Hese, K. M.; de Groot, P. G.; Heijnen, H. F. G.; Sage, E. H.; Williams, S.; McKeown, L.; Gralnick, H. R.; Sixma, J. J. Platelet Adhesion to Collagen Types I through VIII Under Conditions of Stasis and Flow is Mediated by GPIa/IIIa (alpha2beta1-Integrin). *Blood* 1994, 83, 1244-1250.
2. DeWood, M. A. S., J.; Notske, R.; Mouser, L. T.; Burroughs, R.; Golden, M. S.; Lang, K. T. Prevalence of Total Coronary Occlusion During the Early Hours of Transmural Myocardial Infarction. *N. Eng. J. Med.* 1980, 303, 897-902.
3. Rosamond, W. F., K.; Furie, K.; Go, A.; Greenlund, K.; Haase, K.; Hailpern, S. M.; Ho, M.; Howard, V.; Kissela, B.; Kittner, S.; Lloyd-Jones, D.; McDermott, M.; Meigs, J.; Moy, C.; Nichol, G.; O'Donnell, C.; Roger, V.; Sorlie, P.; Steinberger, J.; Thom, T.; Wilson, M; Hong, Y. Heart disease and stroke statistics 2008 update. A report from the American Heart Association. *Circulation* Prepublished online: 2007 Dec. 17, DOI: 10.1161/CIRCULATIONAHA.107.187998.
4. Santoro, S. A. Platelet Surface Collagen Polymorphisms: Variable Receptor Expression and Thrombotic/Hemorrhagic Risk. *Blood* 1999, 93, 3575-3577.
5. Watson, S. P. a. G., J. Collagen receptor signaling in platelets: extending the role of the ITAM. *Immunol. Today* 1998, 19, 260-264.
6. Nieuwenhuis, H. K. A., J. W. N.; Houdijk, W. P. M.; Sixma, J. J. Human blood platelets showing no response to collagen fail to express surface glycoprotein Ia. *Nature* 1985, 318, 470-472.
7. Nieuwenhuis, H. K. S., K. S.; Houdijk, W. P. M.; Nievelstein, P. F. E. M.; Sixma, J. J. Deficiency of platelet membrane glycoprotein Ia associated with a decreased platelet adhesion to subendothelium: a defect in platelet spreading. *Blood* 1986, 68, 692-695.
8. Kehrel, B. B., L.; Kokott, R.; Mesters, R.; Stenzinger, W.; Clemetson, K. J.; van der Loo, J. Deficiency of intact thrombospondin and membrane glycoprotein Ia in platelets with defective collagen-induced aggregation and spontaneous loss of disorder. *Blood* 1988, 71, 1074-1078.
9. Handa, M.; Watanabe, K.; Kawai, Y.; Kamata, T.; Koyama, T.; Nagai, H.; Ikeda, Y. Platelet unresponsiveness to collagen: involvement of glycoprotein Ia-IIa (alpha2beta1 integrin) deficiency associated with a myeloproliferative disorder. *Thromb. Haemost.* 1995, 73, 521-528.
10. Holtkotter, O, N., B.; Smyth, N.; Muller, W.; Hafner, M.; Schulte, V.; Krieg, T.; Eckes, B. Integrin alpha2-deficient mice develop normally, are fertile, but display partially defective platelet interaction with collagen. *J. Biol. Chem.* 2002, 277, 10789-10794.
11. Kunicki, T. J. O., R.; Annis, D.; Honda, Y. Variability of integrin alpha2beta1 activity on human platelets. *Blood* 1993, 82, 2693-2703.
12. Furihata, K. N., D. J.; Kunicki, T. J. Influence of platelet collagen receptor polymorphisms on risk for arterial thrombosis. *Arch. Pathol. Lab. Med.* 2002, 126, 305-309.
13. Emsley, J. K., S. L.; Bergelson, J. M.; Liddington, R. C. Crystal Structure of the I Domain from Integrin alpha2beta1. *J. Biol. Chem.* 1997, 273, 28512-28517.
14. Emsley, J. K., C. G.; Farndale, R. W.; Barnes, M. J.; LIddington, R. C. Structural Basis of Collagen Recognition by Integrin alpha2beta1. *Cell* 2000, 101, 47-56.
15. Takagi, J. P., B. M.; Walz, T.; Springer, T. A. Global conformational rearrangements in integrin extracellular domains in outside-in and inside-out signaling. *Cell* 2002, 110, 599-611.
16. Jung, S. M. a. M., M. Signal-transducing mechanisms involved in activation of the platelet collagen receptor integrin alpha2beta1. *J. Biol. Chem.* 2000, 275, 8016-8026.
17. Connors, W. L. J., J.; White, D. J.; Puranen, J. S.; Kankaanpaa, P.; Upla, P.; Tulla, M.; Johnson, M. S.; Heino, J. Two synergistic activation mechanisms of integrin alpha2beta1 integrin-mediated collagen binding. *J. Biol. Chem.* 2007, 282, 14675-14683.
18. Lu, C. S., M.; Zang, Q.; Takagi, J.; Springer, T. A. Locking in Alternate Conformations of the Integrin aLb2 I Domain with Disulfide Bonds Reveals Functional Relationships Among Integrin Domains. *PNAS* 2001, 98, 2393-2398.
19. Welzenbach, K. H., U.; Weitz-Schmidt, G. Small molecule inhibitors induce conformational changes in the I-domain and the I-like domain of lymphocyte function-associated antigen-1. *J. Biol. Chem.* 2002, 277, 10590-10598.
20. Shimaoka, M. S., A.; Yang, W.; Weitz-Schmidt, G.; Springer, T. A. Small molecule integrin antagonists that bind to the beta2 subunit I-like domain and activate signals in one direction and block them in the other. *Immunity* 2003, 19, 391-402.
21. Luo, B.-H. C., C. V.; Springer, T. A. Structural basis of integrin signaling and regulation. *Annu. Rev. Immunol.* 2007, 25, 619-647.
22. Choi, S. V., G.; Marcinkiewicz, C.; Winkler, J. D.; Bennett, J. S.; DeGrado, W. F. Small Molecule Inhibitors of Integrin alpha2beta1. *J. Med. Chem.* 2007, 50, 5457-5462.
23. Shattil, S. J. a. N., P. J. Integrins: Dynamic Scaffolds for Adhesion and Signaling in Platelets. *Blood* 2004, 104, 1606-1615.
24. Tam, S. H. S., P. M.; Jordan, R. E.; Nakada, M. T. Abciximab (ReoPro, chimeric 7E3 Fab) demonstrates equivalent affinity and functional blockade of glycoprotein IIb/IIIa and alphavbeta3 integrins. *Circulation* 1998, 98, 1085-1091.
25. Bennett, J. S. Structure and function of the platelet integrin alphaIIbbeta3. *J. Clin. Invest.* 2005, 115, 3363-3369.
26. White, T. C. B., M. A.; Robinson, D. K.; Yin, H.; DeGrado, W. F.; Hanson, S. R.; McCarty, O. J. The Leech Product Saratin is a Potent Inhibitor of Platelet Integrin alpha2beta1 and von Willebrand Factor Binding to Collagen. *FEBS J.* 2007, 274, 1481-1491.
27. Bellavite, P. A., G.; Guzzo, P.; Arigliano, P.; Chirumbolo, S.; Manzato, F.; Santonastaso, C. A Colorimetric Method for the Measure of Platelet Adhesion in Microtiter Plates. *Anal Biochem.* 1994, 216, 444-450.
28. Bennett, J. S. C., C.; Vilaire, G.; Mousa, S. A.; DeGrado, W. F. Agonist-Activated alphavbeta3 on Platelets and Lymphocytes Binds to the Matrix Protein Osteopontin. *J. Biol. Chem.* 1997, 272, 8137-8140.
29. Bennett, J. S. a. V., G. Exposure of platelet fibrinogen receptors by ADP and epinephrine. *J. Clin. Invest.* 1979, 64, 1393-1401.

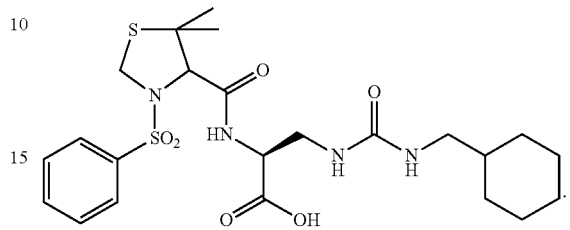

What is claimed:
1. A compound having the formula I

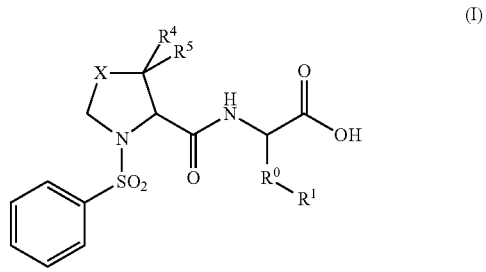

wherein:
X is $CH_2$, N, O, S, or a bond;
$R^0$ is methylene;
$R^1$ is —NHC(=O)$R^2$ or —NHC(=S)$R^2$;
$R^2$ is —NH(CHR$^6$)$R^7$;
$R^4$ and $R^5$ are each independently H or —$CH_3$;

$R^6$ is H, alkyl, or aryl; and, $R^7$ is alkyl, aryl, or aralkyl, or a stereoisomer, partial stereoisomer, pharmaceutically acceptable salt, acid hydrate, or N-oxide thereof.

2. A composition comprising a compound according to claim 1 and a pharmaceutically acceptable carrier, diluent, or excipient.

3. A composition comprising a stereochemically enriched mixture of compounds according to claim 2.

4. The compound according to claim 1 wherein $R^4$ and $R^5$ are each —$CH_3$, X is S, and $R^0$ is —$CH_2$—.

5. The compound according to claim 4 wherein said compound is 2-[(3-Benzenesulfonyl-5,5-dimethyl-thiazolidine-4-carbonyl)-amino]-3-[3-(2,2-dimethyl-propyl)-ureido]-propionic acid.

6. The compound according to claim 4 wherein $R^6$ is H and $R^7$ is aryl or aralkyl.

7. The compound according to claim 6 wherein said compound is
2-[(3-Benzenesulfonyl-5,5-dimethyl-thiazolidine-4-carbonyl)-amino]-3-[3-(2,2-diphenyl-ethyl)-ureido]-propionic acid.

8. The compound according to claim 6 wherein $R^7$ is aryl and $R^1$ is —NHC(=S)$R^2$.

9. The compound according to claim 8 wherein the compound is 2-[(3-Benzenesulfonyl-5,5-dimethyl-thiazolidine-4-carbonyl)-amino]-3-(3-benzyl-thioureido)-propionic acid.

10. The compound according to claim 6 wherein $R^7$ is aralkyl.

11. The compound according to claim 10 wherein said compound is
2-[(3-Benzenesulfonyl-5,5-dimethyl-thiazolidine-4-carbonyl)-amino]-3-(3-phenethyl-ureido)-propionic acid; or,
2-[(3-Benzenesulfonyl-5,5-dimethyl-thiazolidine-4-carbonyl)-amino]-3-[3-(2,2-diphenyl-ethyl)-ureido]-propionic acid.

12. The compound according to claim 6 wherein $R^7$ is phenyl substituted with one or more alkyl, halo, trifluoromethyl, or trifluoromethoxy.

13. The compound according to claim 12 wherein said compound is
2-[(3-Benzenesulfonyl-5,5-dimethyl-thiazolidine-4-carbonyl)-amino]-3-[3-(2-methyl-benzyl)-ureido]-propionic acid;
2-[(3-Benzenesulfonyl-5,5-dimethyl-thiazolidine-4-carbonyl)-amino]-3-[3-(3-methyl-benzyl)-ureido]-propionic acid;
2-[(3-Benzenesulfonyl-5,5-dimethyl-thiazolidine-4-carbonyl)-amino]-3-[3-(4-methyl-benzyl)-ureido]-propionic acid;
2-[(3-Benzenesulfonyl-5,5-dimethyl-thiazolidine-4-carbonyl)-amino]-3-[3-(2,6-difluoro-benzyl)-ureido]-propionic acid;
2-[(3-Benzenesulfonyl-5,5-dimethyl-thiazolidine-4-carbonyl)-amino]-3-[3-(3,5-difluoro-benzyl)-ureido]-propionic acid;
2-[(3-Benzenesulfonyl-5,5-dimethyl-thiazolidine-4-carbonyl)-amino]-3-[3-(4-fluoro-benzyl)-ureido]-propionic acid;
2-[(3-Benzenesulfonyl-5,5-dimethyl-thiazolidine-4-carbonyl)-amino]-3-[3-(4-chloro-benzyl)-ureido]-propionic acid;
2-[(3-Benzenesulfonyl-5,5-dimethyl-thiazolidine-4-carbonyl)-amino]-3-[3-(4-bromo-benzyl)-ureido]-propionic acid;
2-[(3-Benzenesulfonyl-5,5-dimethyl-thiazolidine-4-carbonyl)-amino]-3-[3-(4-trifluoromethoxy-benzyl)-ureido]-propionic acid; or
2-[(3-Benzenesulfonyl-5,5-dimethyl-thiazolidine-4-carbonyl)-amino]-3-[3-(4-trifluoromethyl-benzyl)-ureido]-propionic acid.

14. The compound according to claim 4 wherein $R^6$ is —$CH_3$ and $R^7$ is phenyl.

15. The compound according to claim 14 wherein said compound is 2-[(3-Benzenesulfonyl-5,5-dimethyl-thiazolidine-4-carbonyl)-amino]-3-[3-(1-phenyl-ethyl)-ureido]-propionic acid.

16. The compound according to claim 1 wherein $R^6$ is —H, $R^7$ is phenyl, and X is S or O.

17. The compound according to claim 16 wherein $R^4$ and $R^5$ are both H or are both —$CH_3$.

18. The compound according to claim 17 wherein said compound is
2-[(3-Benzenesulfonyl-thiazolidine-4-carbonyl)-amino]-3-(3-benzyl-ureido)-propionic acid; or,
2-[(3-Benzenesulfonyl-oxazolidine-4-carbonyl)-amino]-3-(3-benzyl-ureido)-propionic acid.

19. The compound according to claim 16 wherein one of $R^4$ and $R^5$ is H, and the other of $R^4$ and $R^5$ is —$CH_3$.

20. The compound according to claim 19 wherein the compound is 2-[(3-Benzenesulfonyl-5-methyl-oxazolidine-4-carbonyl)-amino]-3-(3-benzyl-ureido)-propionic acid.

21. The compound according to claim 1 wherein X is a bond.

22. The compound according to claim 21 wherein the compound is 2-[(1-Benzenesulfonyl-azetidine-2-carbonyl)-amino]-3-(3-benzyl-ureido)-propionic acid.

23. A method for treating at least one integrin α2β1-affected disease state or infection comprising the step of administering to a subject in need thereof a composition comprising a therapeutically effective amount of a compound having the formula II:

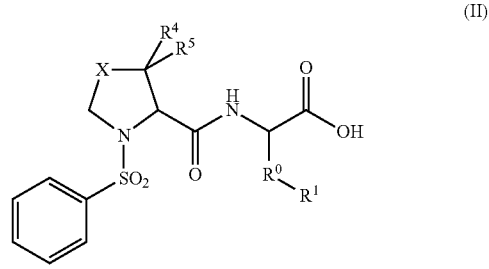

wherein:
X is $CH_2$, N, O, S, or a bond;
$R^0$ is methylene;
$R^1$ is —NHC(=O)$R^2$ or —NHC(=S)$R^2$;
$R^2$ is —NH(CHR$^6$)$R^7$;
$R^4$ and $R^5$ are each independently H or —$CH_3$;
$R^6$ is H, alkyl, or aryl; and,
$R^7$ is alkyl, aryl, or aralkyl, or a stereoisomer, partial stereoisomer, pharmaceutically acceptable salt, acid hydrate, or N-oxide thereof.

24. The method according to claim 23 wherein the subject is suffering from one or more of acute coronary syndromes, stroke, ischaemic complications of peripheral vascular disease, deep vein thrombosis (DVT), myocardial infarction, coronary artery disease, cerebrovascular disease, peripheral arterial disease, diabetes mellitus, atrial fibrillation, congestive heart failure, and pulmonary embolism.

25. The method according to claim 23, wherein the subject is suffering from human melanoma or hepatocellular carcinoma.

26. The method according to claim 23, wherein the subject is suffering from rheumatoid arthritis or diabetic retinopathy.

27. The method according to claim 23, wherein the disease state or infection is matrix reorganization-affected, angiogenesis-affected, cell migration-, cell proliferation-, cell colonization-, or metastasis-affected, leukocyte infiltration-affected, edema-affected, or any combination thereof.

28. The method according to claim 23, wherein the disease state or infection is angiogenesis-affected.

29. The method according to claim 23, where in the subject is suffering from viral infection.

30. The method according to claim 23, wherein said viral infection is at least partially attributable to human cytomegalovirus (HCMV), rotaviruses, Piconaviridae viruses, or related viruses.

31. The method according to claim 23 wherein said composition additionally comprises a pharmaceutically acceptable carrier, diluent, or excipient.

32. The method according to claim 23, wherein said composition comprises a stereochemically enriched mixture of compounds of the formula II.

33. The method according to claim 23, wherein said subject is human.

34. A compound, wherein said compound is: